United States Patent
Shin et al.

(10) Patent No.: US 11,142,509 B2
(45) Date of Patent: Oct. 12, 2021

(54) INTERMEDIATE FOR PREPARING ERIBULIN MESYLATE AND PROCESS FOR PREPARING THE SAME

(71) Applicant: YONSUNG FINE CHEMICAL CO., LTD., Gyeonggi-do (KR)

(72) Inventors: Hyunik Shin, Suwon-si (KR); Keeyoung Lee, Seoul (KR); Changyoung Oh, Seongnam-si (KR)

(73) Assignee: YONSUNG FINE CHEMICAL CO., LTD., Hwaseong-si (KR)

( * ) Notice: Subject to any disclaimer, the term of this patent is extended or adjusted under 35 U.S.C. 154(b) by 0 days.

(21) Appl. No.: 16/762,355

(22) PCT Filed: Nov. 8, 2018

(86) PCT No.: PCT/KR2018/013510
§ 371 (c)(1),
(2) Date: May 7, 2020

(87) PCT Pub. No.: WO2019/093776
PCT Pub. Date: May 16, 2019

(65) Prior Publication Data
US 2020/0361890 A1    Nov. 19, 2020

(30) Foreign Application Priority Data
Nov. 9, 2017  (KR) .................. 10-2017-0149015

(51) Int. Cl.
*C07D 407/12*    (2006.01)
*C07D 307/12*    (2006.01)

(52) U.S. Cl.
CPC ......... *C07D 307/12* (2013.01); *C07D 407/12* (2013.01)

(58) Field of Classification Search
CPC .. C07D 307/12; C07D 407/12; C07D 493/22; Y02P 20/55; A61K 31/357
USPC ........................................ 549/214
See application file for complete search history.

(56) References Cited

U.S. PATENT DOCUMENTS

| | | | |
|---|---|---|---|
| 6,214,865 B1 | 4/2001 | Littlefield et al. | |
| 6,365,759 B1 | 4/2002 | Littlefield et al. | |
| 7,982,060 B2 | 7/2011 | Austad et al. | |

FOREIGN PATENT DOCUMENTS

WO    2006/076100 A2    7/2006

OTHER PUBLICATIONS

Austad, Brian C. et al., "Process Development of Halaven®: Synthesis of the C14-C35 Fragment via Iterative Nozaki-Hiyama-Kishi Reaction-Williamson Ether Cyclization", Synlett, 2013, pp. 327-332, vol. 24.
Prabhakar, P. et al., "A Mild and Efficient Chemoselective Protection of Primary Alcohols as Pivaloyl Esters Using La(NO$_3$)$_3$•6H$_2$O as a Catalyst under Solvent-free Conditions", Chemistry Letters, 2007, pp. 732-733, vol. 36, No. 6.
International Search Report of PCT/KR2018/013510 dated Feb. 18, 2019 [PCT/ISA/210] English Translation.

*Primary Examiner* — Taylor V Oh
(74) *Attorney, Agent, or Firm* — Sughrue Mion, PLLC

(57) ABSTRACT

The present invention relates to a process for preparing a compound of formula (6) which is an intermediate for the preparation of eribulin mesylate with high yields and high purity, and an intermediate therefor.

13 Claims, No Drawings

INTERMEDIATE FOR PREPARING ERIBULIN MESYLATE AND PROCESS FOR PREPARING THE SAME

CROSS REFERENCE TO RELATED APPLICATIONS

This application is a National Stage of International Application No. PCT/KR2018/013510, filed Nov. 8, 2018, claiming priority to Korean Patent Application No. 10-2017-0149015, filed Nov. 9, 2017.

TECHNICAL FIELD

The present invention relates to a novel intermediate for the preparation of eribulin mesylate and a process for preparing the same.

BACKGROUND ART

Eribulin mesylate represented by the following formula (1) is an active pharmaceutical ingredient (API) of Halaven which is a medicine for breast cancer.

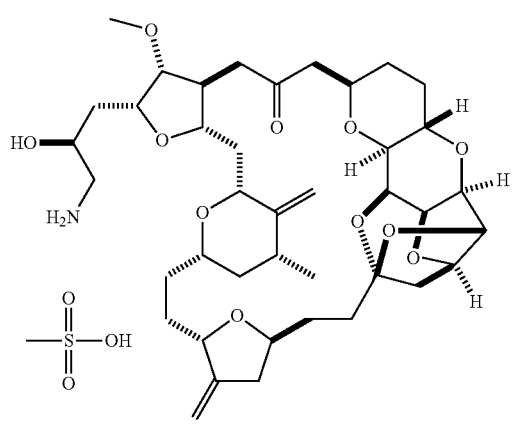

(1)

U.S. Pat. No. 6,214,865 discloses a process for preparing eribulin mesylate of formula (1) using the compound of the following formula (2) as a key intermediate, as shown in the following reaction scheme 1.

[Reaction Scheme 1]

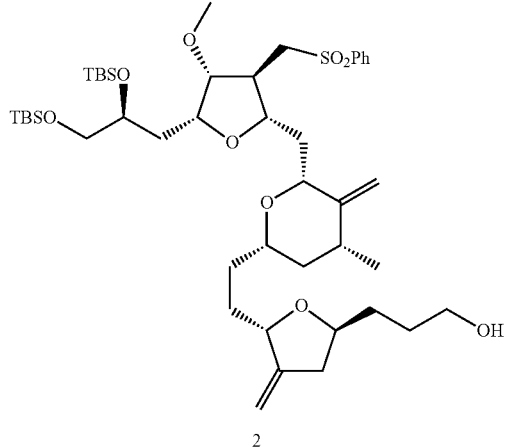

2

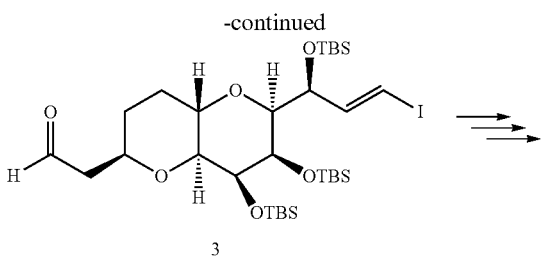

3

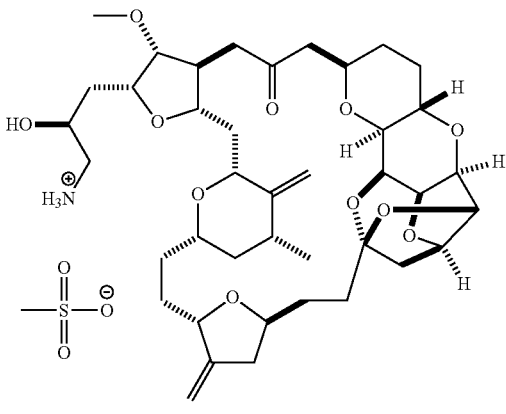

1

Also, as shown in the following reaction scheme 2, a process for preparing the compound of formula (2) using the compound of the following formula (4) is disclosed.

[Reaction Scheme 2]

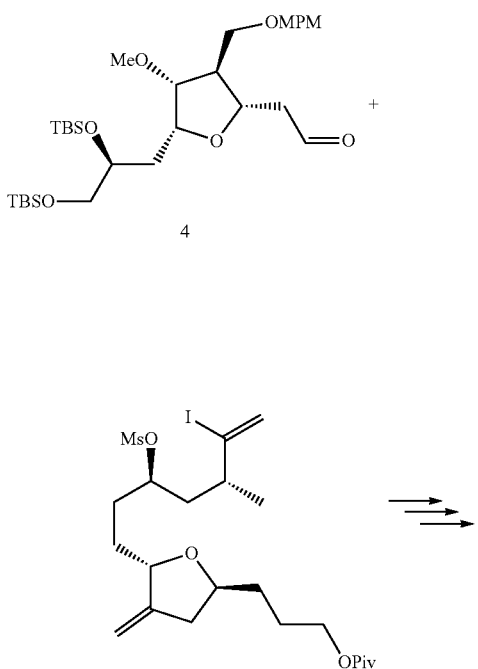

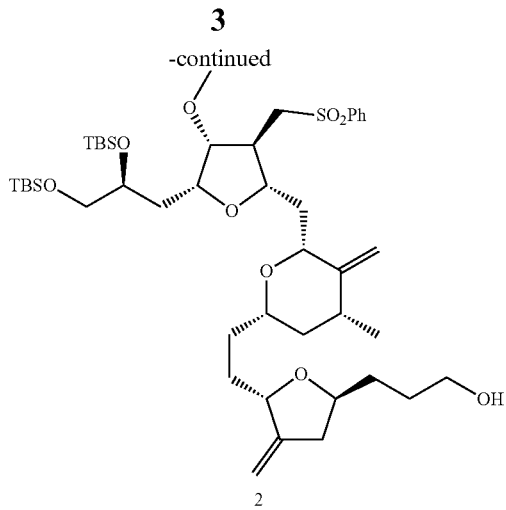

2

However, the above process has problems of long synthesis pathway and low yields.

Meanwhile, U.S. Pat. No. 7,982,060 discloses a process for preparing the compound of formula (2) using the compound of the following formula (5), as shown in the following reaction scheme 3.

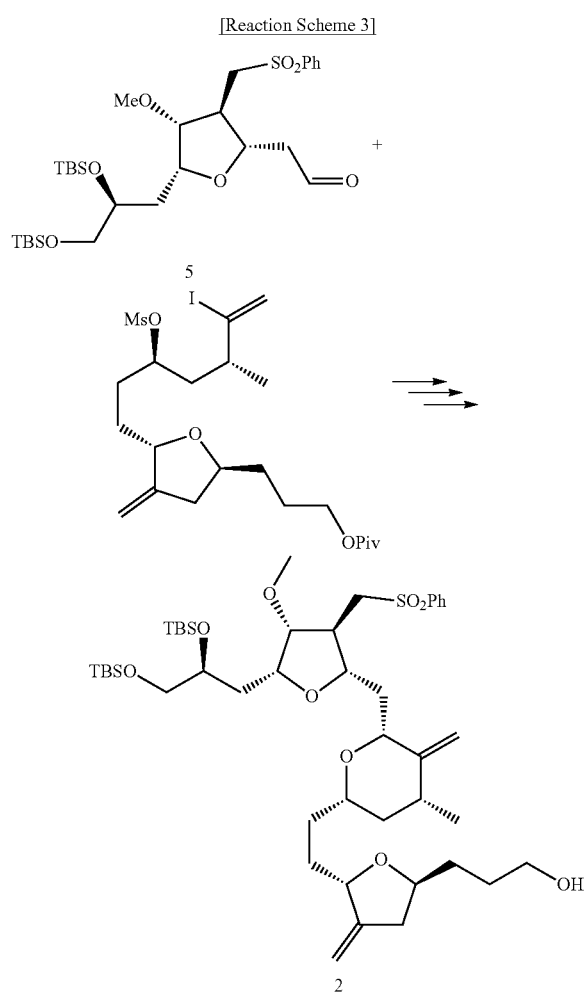

However, the above process has problems that the preparation process is complicated and the yield is lowered.

DISCLOSURE

Technical Problem

The present inventors have endeavored to overcome the above problems in the preparation of the compound of formula (2) which is a key intermediate for eribulin mesylate, and found that the compound of formula (2) can be prepared with high yields and high purity using a compound of the following formula (6) to complete the present invention.

An object of the present invention is, therefore, to provide the compound of the following formula (6) which is an intermediate for the preparation of eribulin mesylate.

Another object of the present invention is to provide a process for preparing the compound of formula (6) with high yields and high purity.

Still another object of the present invention is to provide an intermediate used in the above preparation process.

Still another object of the present invention is to provide an intermediate used in the process for preparing the compound of formula (2) using the compound of formula (6).

Technical Solution

One embodiment of the present invention relates to a compound of the following formula (6) which is an intermediate for the preparation of eribulin mesylate.

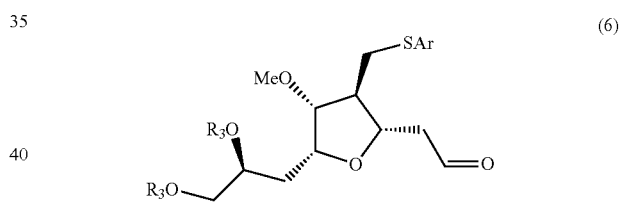

(6)

wherein, $R_3$ represents a silyl protecting group, particularly t-butyldimethylsilyl, and Ar represents aryl, particularly phenyl.

The term "silyl protecting group" as used herein includes trimethylsilyl (TMS), triethylsilyl (TES), t-butyldimethylsilyl (TBS), t-butyldiphenylsilyl (TBDPS), etc., but is not limited thereto.

The term "aryl" as used herein includes all of an aromatic group, heteroaromatic group, and partially reduced derivatives thereof. The aromatic group means a 5- to 15-membered simple or fused ring, and the heteroaromatic group means an aromatic group comprising at least one of oxygen, sulfur or nitrogen. Typical examples of the aryl group include phenyl, benzyl, naphthyl, pyridinyl, furanyl, thiophenyl, indolyl, quinolinyl, imidazolinyl, oxazolyl, thiazolyl, tetrahydronaphthyl, etc., but are not limited thereto.

One embodiment of the present invention relates to a process for preparing the compound of formula (6), which comprises the steps of:

(i) subjecting a primary hydroxy group of a compound of the following formula (7) to selective sulfonylation to obtain a compound of the following formula (8);

(ii) subjecting the compound of the following formula (8) to cyclization to obtain a compound of the following formula (9);
(iii) subjecting the compound of the following formula (9) to allylation to obtain a compound of the following formula (10);
(iv) subjecting a hydroxy group of the compound of the following formula (10) to methylation to obtain a compound of the following formula (11);
(v) subjecting an alkene group of the compound of the following formula (11) to stereoselective dehydroxylation to obtain a compound of the following formula (12);
(vi) protecting a hydroxy group of the compound of the following formula (12) to obtain a compound of the following formula (13);
(vii) subjecting the compound of the following formula (13) to Hosomi-Sakurai reaction to obtain a compound of the following formula (14);
(viii) subjecting an alkene group of the compound of the following formula (14) to dehydroxylation, oxidation and reduction to obtain a compound of the following formula (15);
(ix) selectively protecting a primary hydroxy group of the compound of the following formula (15) to obtain a compound of the following formula (16);
(x) oxidizing a hydroxy group of the compound of the following formula (16) to obtain a compound of the following formula (17);
(xi) subjecting the compound of the following formula (17) to methenylation to obtain a compound of the following formula (18);
(xii) subjecting the compound of the following formula (18) to hydroboration and oxidation to obtain a compound of the following formula (19);
(xiii) oxidizing a hydroxy group of the compound of the following formula (19) to obtain a compound of the following formula (20);
(xiv) subjecting the compound of the following formula (20) to isomerization to obtain a compound of the following formula (21);
(xv) reducing the compound of the following formula (21) to obtain a compound of the following formula (22);
(xvi) subjecting a hydroxy group of the compound of the following formula (22) to sulfonylation to obtain a compound of the following formula (23);
(xvii) substituting a leaving group of the compound of the following formula (23) with a sulfide to obtain a compound of the following formula (24);
(xviii) selectively deprotecting a benzoyl or acetyl group of the compound of the following formula (24) to obtain a compound of the following formula (25);
(xix) protecting a hydroxy group of the compound of the following formula (25) to obtain a compound of the following formula (26);
(xx) deprotecting a pivaloyl group of the compound of the following formula (26) to obtain a compound of the following formula (27); and
(xxi) oxidizing a hydroxy group of the compound of the following formula (27).

(7)

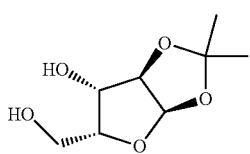

-continued (8)

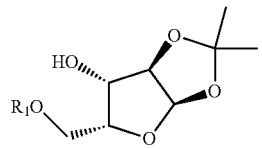

(9)

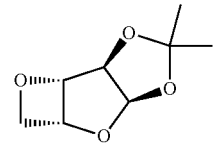

(10)

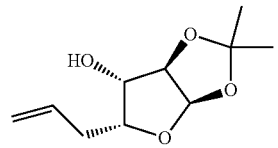

(11)

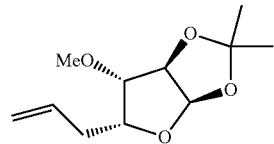

(12)

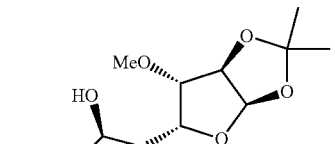

(13)

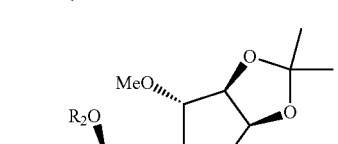

(14)

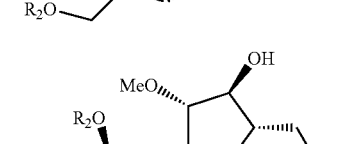

(15)

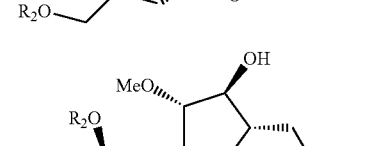

(16)

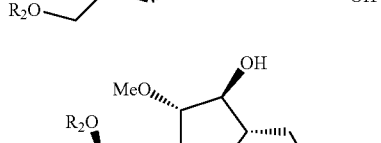

(17)

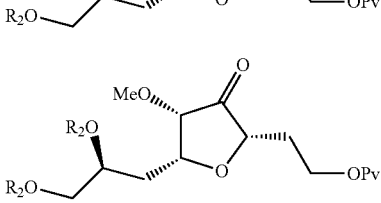

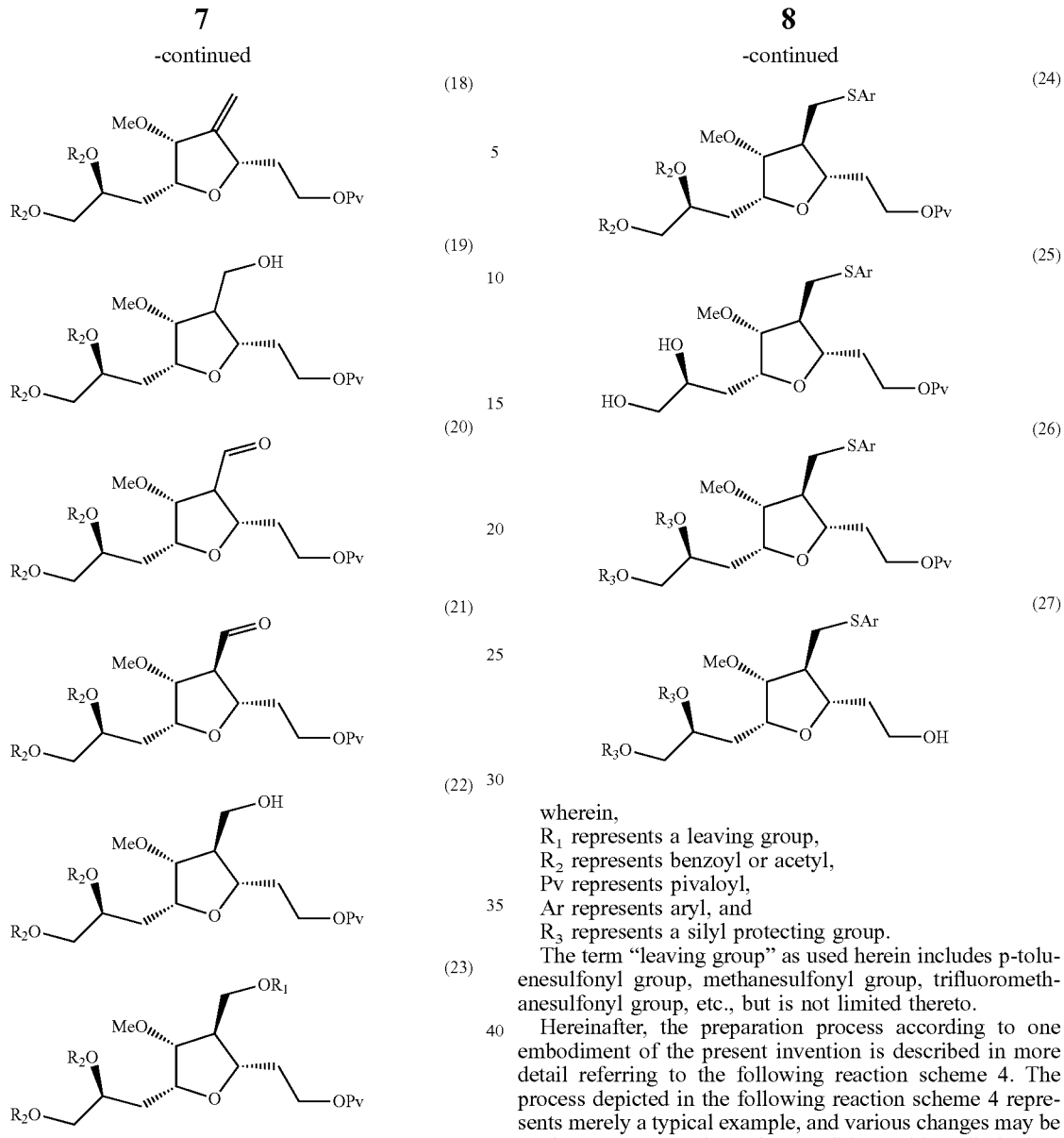

wherein,
R$_1$ represents a leaving group,
R$_2$ represents benzoyl or acetyl,
Pv represents pivaloyl,
Ar represents aryl, and
R$_3$ represents a silyl protecting group.

The term "leaving group" as used herein includes p-toluenesulfonyl group, methanesulfonyl group, trifluoromethanesulfonyl group, etc., but is not limited thereto.

Hereinafter, the preparation process according to one embodiment of the present invention is described in more detail referring to the following reaction scheme 4. The process depicted in the following reaction scheme 4 represents merely a typical example, and various changes may be made to reagents and reaction conditions without limitation.

[Reaction Scheme 4]

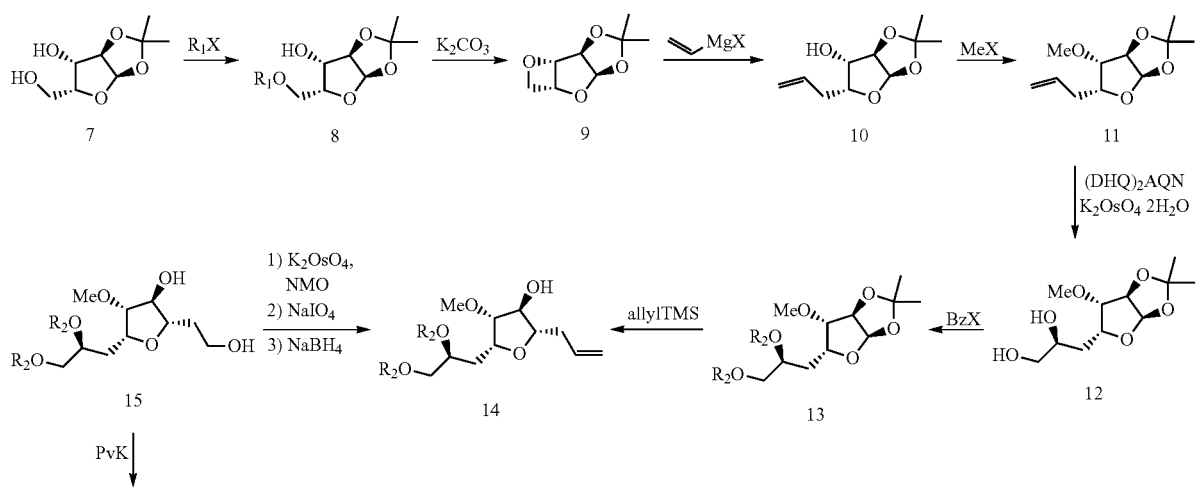

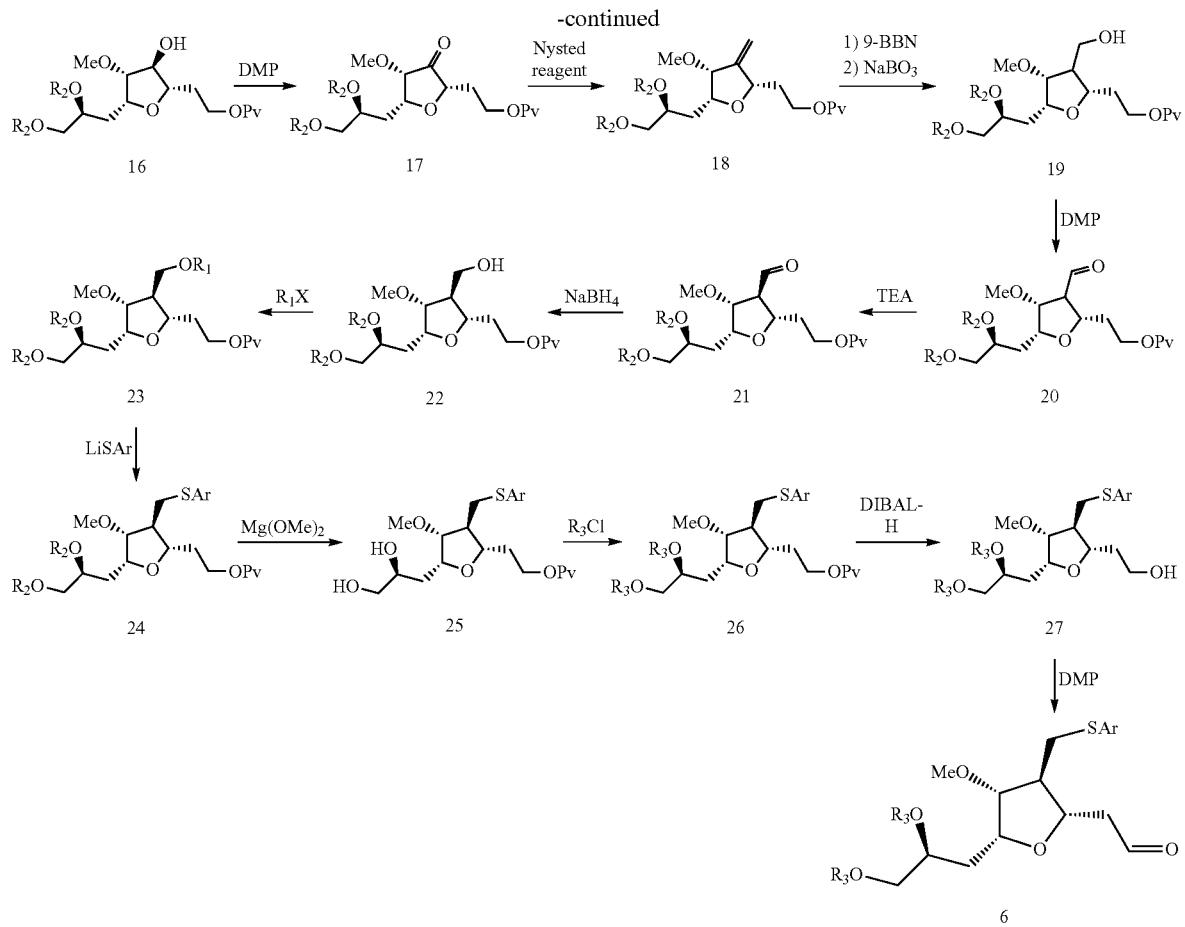

Step 1: Synthesis of Compound of Formula (8)

The compound of formula (8) can be obtained by subjecting a primary hydroxy group of the compound of formula (7) to selective sulfonylation.

The sulfonylation may be carried out by reacting the compound of formula (7) with p-toluenesulfonyl halide, methanesulfonyl halide, trifluoromethanesulfonic anhydride, etc. under a basic condition.

As the base, triethylamine, 4-dimethylaminopyridine, pyridine, etc. may be used. Particularly, triethylamine is preferred.

As a reaction solvent, methylenechloride, chloroform, tetrahydrofuran, etc. may be used. Particularly, methylenechloride is preferred.

The reaction is preferably performed at room temperature.

In accordance with one embodiment of the present invention, the obtained compound of formula (8) is recrystalized with heptance and toluene for purification. The recrystalization can be performed by adding toluene to the compound of formula (8), followed by heating to 50° C. and cooling to 20 to 30° C., and then adding heptane thereto.

Step 2: Synthesis of Compound of Formula (9)

The compound of formula (9) can be obtained by subjecting the compound of formula (8) to cyclization under a basic condition.

As the base, potassium carbonate, sodium carbonate, cesium carbonate, etc. may be used. Particularly, potassium carbonate is preferred.

As a reaction solvent, methanol, ethanol, isopropanol, etc. may be used. Particularly, methanol is preferred.

The reaction is preferably performed at about 45 to 50° C.

Step 3: Synthesis of Compound of Formula (10)

The compound of formula (10) can be obtained by subjecting the compound of formula (9) to allylation.

The allylation may be carried out using a Grignard reagent, such as vinyl magnesium bromide, vinyl magnesium chloride, etc.

As a reaction solvent, methylenechloride, chloroform, tetrahydrofuran, etc. may be used. Particularly, tetrahydrofuran is preferred.

The reaction is preferably performed under a reflux condition.

In accordance with one embodiment of the present invention, the obtained compound of formula (10) is recrystalized with heptane and toluene for purification. The recrystalization can be performed by adding heptane and toluene to the compound of formula (10), heating at 50° C., and then cooling to 20° C.

Step 4: Synthesis of Compound of Formula (11)

The compound of formula (11) can be obtained by subjecting a hydroxy group of the compound of formula (10) to methylation.

The methylation may be carried out by reacting the compound of formula (10) with methyl halide, such as iodomethane, under a basic condition.

As the base, sodium hydride, lithium hydride, etc. may be used. Particularly, sodium hydride is preferred.

As a reaction solvent, tetrahydrofuran, dimethylformamide, etc. may be used. Particularly, dimethylformamide is preferred.

The reaction is preferably performed at room temperature.

Step 5: Synthesis of Compound of Formula (12)

The compound of formula (12) can be obtained by subjecting an alkene group of the compound of formula (11) to stereoselective dehydroxylation.

The dehydroxylation may be carried out using a chiral reagent and oxidant.

As the chiral reagent, hydroquinine anthraquinone-1,4-diyl diether ((DHQ)$_2$AQN), hydroquinidine anthraquinone-1,4-diyl diether ((DHQD)$_2$AQN), etc. may be used. Particularly, hydroquinine anthraquinone-1,4-diyl diether is preferred.

As the oxidant, potassium osmate ($K_2OsO_4$), osumium tetraoxide ($OsO_4$), etc. may be used. Particularly, potassium osmate is preferred.

As a reaction solvent, a mixture solvent of butanol and water is preferred.

The reaction is preferably performed at about 0° C.

Step 6: Synthesis of Compound of Formula (13)

The compound of formula (13) can be obtained by protecting a hydroxy group of the compound of formula (12).

The protection may be carried out by reacting the compound of formula (12) with benzoyl halide or acetyl halide under a basic condition.

As the base, N-methylmorpholine, triethylamine, potassium carbonate, 4-dimethylaminopyridine, etc. may be used. Particularly, N-methylmorpholine and 4-dimethylaminopyridine are preferred.

As a reaction solvent, toluene, dimethylformamide, etc. may be used. Particularly, toluene is preferred.

The reaction is preferably performed at about 75° C.

Step 7: Synthesis of Compound of Formula (14)

The compound of formula (14) can be obtained by subjecting the compound of formula (13) to Hosomi-Sakurai reaction.

The Hosomi-Sakurai reaction may be carried out by reacting the compound of formula (13) with an allylsilane, such as allyltrimethylsilane, in the presence of a Lewis acid.

As the Lewis acid, titanium chloride, boron trifluoride diethyl ether, etc. may be used. Particularly, titanium chloride is preferred.

As a reaction solvent, toluene, methylenechloride, chloroform, etc. may be used. Particularly, toluene is preferred.

The reaction is preferably performed at room temperature.

In accordance with one embodiment of the present invention, the obtained compound of formula (14) is recrystalized with alcohol and heptane for purification. The recrystalization can be performed by adding alcohol to the compound of formula (14), heating at 60° C., and then adding heptane thereto, followed by cooling to 20° C.

Step 8: Synthesis of Compound of Formula (15)

The compound of formula (15) can be obtained by subjecting an alkene group of the compound of formula (14) to dehydroxylation, oxidation and reduction.

The dehydroxylation may be carried out using potassium osmate.

As a reaction solvent, a mixture solvent of water and acetonitrile is preferred, and the reaction is preferably performed at room temperature.

The oxidation may be carried out using sodium periodate ($NaIO_4$), lead tetraacetate ($Pb(C_2H_3O_2)_4$), etc. Particularly, sodium periodate is preferred.

As a reaction solvent, a mixture solvent of methylenechloride and saturated sodium hydrogen carbonate solution is preferred, and the reaction is preferably performed at room temperature.

The reduction may be carried out using sodium borohydride.

As a reaction solvent, methanol, ethanol, isopropanol, etc. may be used. Particularly, methanol is preferred.

The reaction is preferably performed at −5 to 5° C.

Step 9: Synthesis of Compound of Formula (16)

The compound of formula (16) can be obtained by selectively protecting a primary hydroxy group of the compound of formula (15).

The protection may be carried out by reacting the compound of formula (15) with pivaloyl halide, particularly pivaloyl chloride, pivaloyl bromide, pivaloyl iodide, etc. under a basic condition.

As the base, pyridine, triethylamine, 4-methylaminopyridine, etc. may be used. Particularly, pyridine is preferred.

As a reaction solvent, tetrahydrofuran, methylenechloride, chloroform, etc. may be used. Particularly, methylenechloride is preferred.

The reaction is preferably performed at room temperature.

Step 10: Synthesis of Compound of Formula (17)

The compound of formula (17) can be obtained by oxidizing a hydroxy group of the compound of formula (16).

The oxidation may be carried out in the presene of an oxidant such as Dess-Martin periodinane (DMP).

As a reaction solvent, methylenechloride, chloroform, etc. may be used. Particularly, methylenechloride is preferred.

The reaction is preferably performed at room temperature.

Step 11: Synthesis of Compound of Formula (18)

The compound of formula (18) can be obtained by subjecting the compound of formula (17) to methenylation.

The methenylation may be carried out using Wittig reaction, Tebbe reaction, Nysted reaction, etc., but is not limited thereto. Particularly, a Nysted reagent is preferably used.

As a reaction solvent, tetrahydrofuran is preferred.

The reaction is preferably performed at room temperature.

Step 12: Synthesis of Compound of Formula (19)

The compound of formula (19) can be obtained by subjecting the compound of formula (18) to hydroboration and oxidation.

The hydroboration may be carried out using borane, thexylborane, 9-BBN, etc. Particularly, thexylborane is preferred.

As a reaction solvent, tetrahydrofuran is preferred, and the reaction is preferably performed at −5 to 0° C.

The oxidation may be carried out using hydrogen peroxide, sodium perborate, etc. Particularly, sodium perborate is preferred.

The reaction is preferably performed at room temperature.

Step 13: Synthesis of Compound of Formula (20)

The compound of formula (20) can be obtained by oxidizing a hydroxy group of the compound of formula (19).

The oxidation may be carried out in the presence of an oxidant such as Dess-Martin periodinane (DMP).

As a reaction solvent, methylenechloride, chloroform, etc. may be used. Particularly, methylenechloride is preferred.

The reaction is preferably performed at room temperature.

Step 14: Synthesis of Compound of Formula (21)

The compound of formula (21) can be obtained by subjecting the compound of formula (20) to isomerization.

The isomerization may be carried out in the presence of a base.

As the base, triethylamine, 4-dimethylaminopyridine, 1,8-diazabicyclo[5.4.0]undec-7-ene (DBU), etc. may be used. Particularly, triethylamine is preferred.

As a reaction solvent, methylenechloride, chloroform, etc. may be used. Particularly, methylenechloride is preferred.

The reaction is preferably performed at about 30 to 35° C.

Step 15: Synthesis of Compound of Formula (22)

The compound of formula (22) can be obtained by reducing the compound of formula (21).

The reduction may be carried out using sodium borohydride, lithium borohydride, etc. Particularly, sodium borohydride is preferred.

As a reaction solvent, methanol, ethanol, isopropanol, etc. may be used. Particularly, methanol is preferred.

The reaction is preferably performed at 0° C.

Step 16: Synthesis of Compound of Formula (23)

The compound of formula (23) can be obtained by subjecting a hydroxy group of the compound of formula (22) to sulfonylation.

The sulfonylation may be carried out by reacting the compound of formula (22) with p-toluenesulfonyl halide, methanesulfonyl halide, trifluoromethanesulfonic anhydride, etc. under a basic condition.

As the base, triethylamine, 4-dimethylaminopyridine, pyridine, etc. may be used. Particularly, pyridine is preferred.

As a reaction solvent, methylenechloride, chloroform, tetrahydrofuran, etc. may be used. Particularly, methylenechloride is preferred.

The reaction is preferably performed at 0° C.

Step 17: Synthesis of Compound of Formula (24)

The compound of formula (24) can be obtained by substituting a leaving group of the compound of formula (23) with a sulfide.

The substitution may be carried out using lithium thiophenolate, sodium thiophoenolate, sodium p-thiocresolate, sodium 4-methoxyphenylthiolate, sodium 2-naphthalene thiolate, sodium quinolin-8-thiolate, etc.

As a reaction solvent, methylenechloride, chloroform, tetrahydrofuran, etc. may be used. Particularly, tetrahydrofuran is preferred.

The reaction is preferably performed at 0° C.

Step 18: Synthesis of Compound of Formula (25)

The compound of formula (25) can be obtained by selectively deprotecting a benzoyl or acetyl group of the compound of formula (24).

The deprotection may be carried out under a basic condition.

As the base, magnesium methoxide, sodium methoxide, sodium hydroxide, etc. may be used. Particularly, magnesium methoxide is preferred.

As a reaction solvent, methanol, ethanol, isopropanol, etc. may be used. Particularly, methanol is preferred.

The reaction is preferably performed at room temperature.

Step 19: Synthesis of Compound of Formula (26)

The compound of formula (26) can be obtained by protecting a hydroxy group of the compound of formula (25).

The protection may be carried out by reacting the compound of formula (25) with t-butyl di methylsilyl chloride, tri ethyl s ilyl trifluoromethanesulfonate, chlorotriethylsilane, etc. under a basic condition.

As the base, imidazole, triethylamine, 4-dimethylaminopyridine, etc. may be used. Particularly, imidazole is preferred.

As a reaction solvent, methylenechloride, chloroform, dimethylformamide, etc. may be used. Particularly, methylenechloride is preferred.

The reaction is preferably performed at room temperature.

Step 20: Synthesis of Compound of Formula (27)

The compound of formula (27) can be obtained by deprotecting a pivaloyl group of the compound of formula (26).

The deprotection may be carried out using lithium aluminum hydride, sodium bis(2-methoxyethoxy)aluminum dihydride, diisobutylaluminum hydride (DIBAL-H), etc. Particularly, diisobutylaluminum hydride is preferred.

As a reaction solvent, methylenechloride, toluene, tetrahydrofuran, etc. may be used. Particularly, tetrahydrofuran is preferred.

The reaction is preferably performed at −5 to 0° C.

Step 21: Synthesis of Compound of Formula (6)

The compound of formula (6) can be obtained by oxidizing a hydroxy group of the compound of formula (27).

The oxidation may be carried out in the presence of an oxidant such as Dess-Martin periodinane (DMP).

As a reaction solvent, methylenechloride, chloroform, etc. may be used. Particularly, methylenechloride is preferred.

The reaction is preferably performed at room temperature.

One embodiment of the present invention relates to a compound of the following formula (26) which is an intermediate for preparing the compound of formula (6).

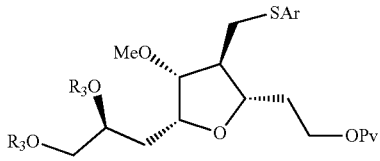

(26)

wherein,

Pv represents pivaloyl, $R_3$ represents a silyl protecting group, particularly t-butyldimethylsilyl, and Ar represents aryl, particularly phenyl.

One embodiment of the present invention relates to a compound of the following formula (27) which is an intermediate for preparing the compound of formula (6).

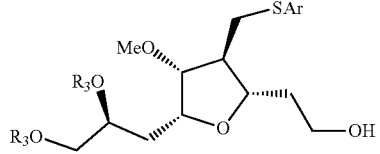

(27)

wherein, $R_3$ represents a silyl protecting group, particularly t-butyldimethylsilyl, and Ar represents aryl, particularly phenyl.

The compound of formula (6) according to one embodiment of the present invention can be effectively used for preparing the compound of formula (2) which is a key intermediate for the preparation of eribulin mesylate.

Accordingly, one embodiment of the present invention relates to a process for preparing a compound of the following formula (2), which comprises the steps of:

(xxii) subjecting a compound of the following formula (6) to Nozaki-Hiyama-Kishi reaction with a compound of the following formula (28) to obtain a compound of the following formula (29);

(xxiii) subjecting the compound of the following formula (29) to cyclization to obtain a compound of the following formula (30);

(xxiv) oxidizing the compound of the following formula (30) to obtain a compound of the following formula (31); and (xxv) deprotecting a pivaloyl group of the compound of the following formula (31).

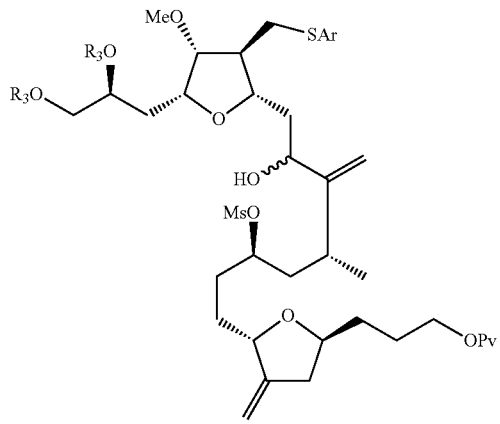

(29)

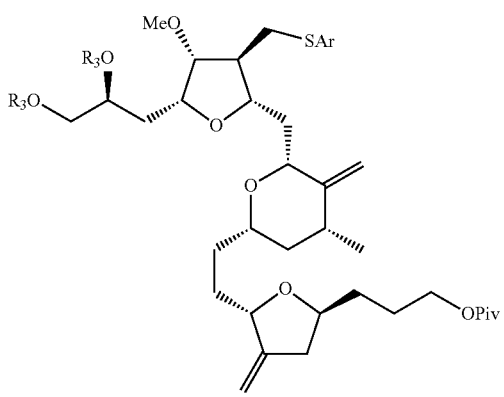

(30)

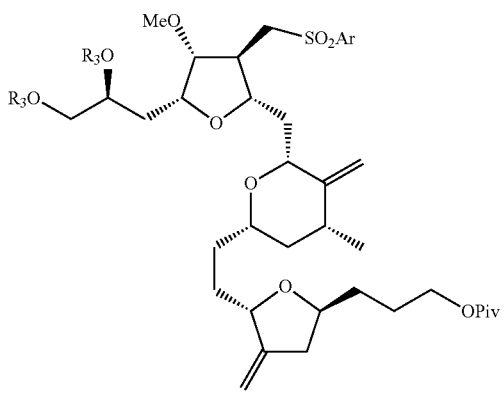

(31)

(2)

(6)

(28)

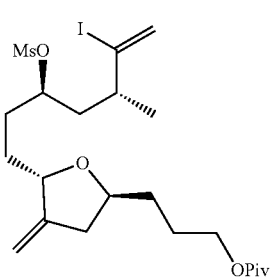

wherein, $R_3$ represents a silyl protecting group,

Ar represents aryl,

Ms represents methanesulfonyl, and

Pv represents pivaloyl.

Hereinafter, the preparation process according to one embodiment of the present invention is described in more detail referring to the following reaction scheme 5. The process depicted in the following reaction scheme 5 represents merely a typical example, and various changes may be made to reagents and reaction conditions without limitation.

[Reaction Scheme 5]

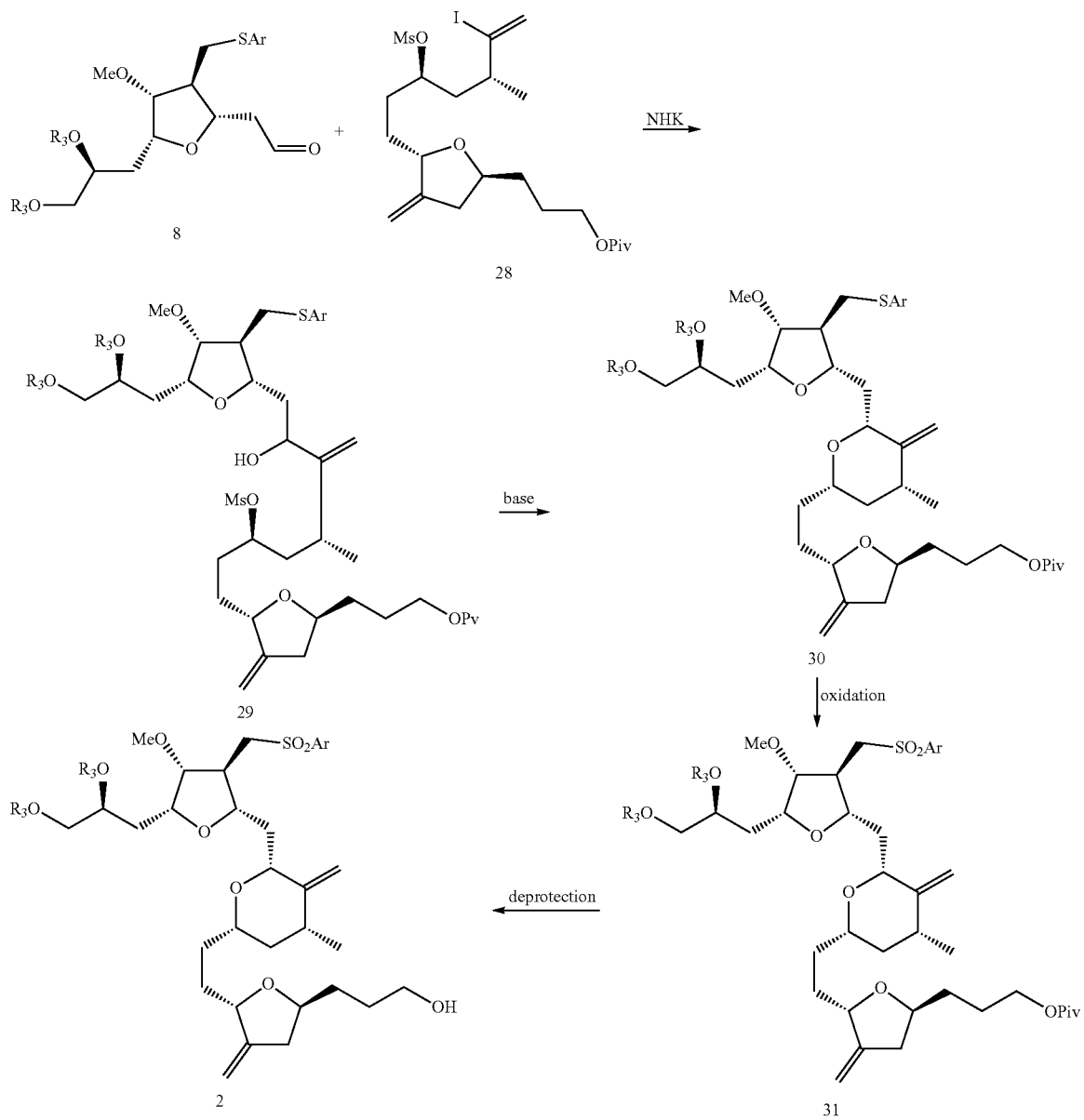

Step 22: Synthesis of Compound of Formula (29)

The compound of formula (29) can be obtained by subjecting the compound of formula (6) to Nozaki-Hiyama-Kishi reaction with the compound of formula (28).

The Nozaki-Hiyama-Kishi reaction may be carried out in the presence of chromium(II) chloride, nickel(II) chloride, a base, and a ligand.

As the base, triethylamine, proton sponge, etc. may be used. Particularly, triethylamine is preferred.

As the ligand, (S)-N-(2-(4-isopropyl-4,5-dihydrooxazol-2-yl)-6-methylphenyl)methane sulfonimide, (S)-N-(2-(4-isopropyl-4,5-dihydrooxazol-2-yl)-6-methoxyphenyl)methane sulfonimide, etc. may be used. Particularly, (S)-N-(2-(4-isopropyl-4,5-dihydrooxazol-2-yl)-6-methylphenyl) methane sulfonimide is preferred.

As a reaction solvent, methylenechloride, acetonitrile, tetrahydrofuran, dimethoxyethane, etc. may be used. Particularly, a mixture solvent of tetrahydrofuran and dimethoxyethane is preferred.

The reaction is preferably performed at about 10 to 35° C.

Step 23: Synthesis of Compound of Formula (30)

The compound of formula (30) can be obtained by subjecting the compound of formula (29) to cyclization under a basic condition.

As the base, lithium bis(trimethylsilyl)amide, sodium bis(trimethylsilyl)amide, potassium bis(trimethylsilyl) amide, etc. may be used. Particularly, potassium bis(trimethylsilyl)amide is preferred.

As a reaction solvent, toluene, tetrahydrofuran, methyl t-butyl ether, etc. may be used. Particularly, tetrahydrofuran is preferred.

The reaction is preferably performed at about −20° C.

Step 24: Synthesis of Compound of Formula (31)

The compound of formula (31) can be obtained by oxidizing the compound of formula (30).

The oxidation may be carried out using 3-chloroperbenzoic acid, hydrogen peroxide, urea hydrogen peroxide, etc. Particularly, urea hydrogen peroxide is preferred.

As a reaction solvent, methanol, ethanol, isopropanol, etc. may be used. Particularly, ethanol is preferred.

The reaction is preferably performed at room temperature.

Step 25: Synthesis of Compound of Formula (2)

The compound of formula (2) can be obtained by deprotecting a pivaloyl group of the compound of formula (31).

The deprotection may be carried out using lithium aluminum tetrahydride, sodium bis(2-methoxyethoxy)aluminum dihydride, diisobutylaluminum hydride (DIBAL-H), etc. Particularly, diisobutylaluminum hydride is preferred.

As a reaction solvent, methylenechloride, tetrahydrofuran, toluene, etc. may be used. Particularly, toluene is preferred.

The reaction is preferably performed at −65° C. or lower.

One embodiment of the present invention relates to a compound of the following formula (29) which is an intermediate for preparing the compound of formula (2).

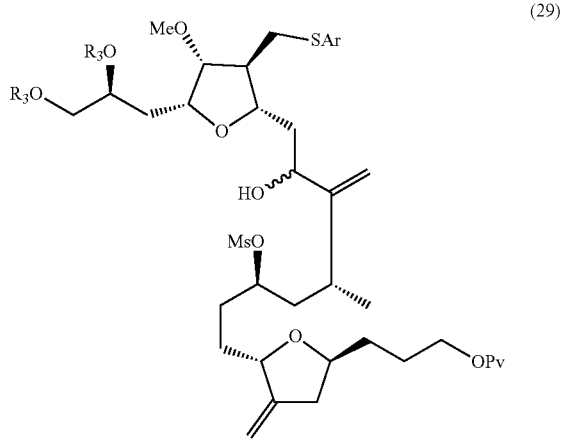

(29)

wherein,
$R_3$ represents a silyl protecting group, particularly t-butyldimethylsilyl,
Ar represents aryl, particularly phenyl,
Ms represents methansulfonyl, and
Pv represents pivaloyl.

Advantageous Effects

In accordance with the preparation process of the present invention, the compound of formula (6) which is a novel intermediate for the preparation of eribulin mesylate can be prepared with high yields and high purity. Further, the compound of formula (2) can be prepared with high yields and high purity using the compound of formula (6).

BEST MODE

Hereinafter, the present invention will be described in more detail by the following examples. It will be obvious to those skilled in the art that these examples are merely described for illustration of the present invention and the scope of the present invention is not limited thereto.

Example 1

Preparation of Compound of Formula (8a)

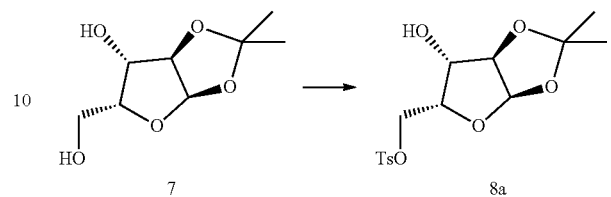

The compound of formula (7) (33 kg) was added to methylenechloride (330 L) for dissolution, followed by cooling to 0° C. Triethylamine (21.07 kg) was added thereto, with maintaining the temperature of 5° C. or lower. p-Toluenesulfonyl chloride (36.89 kg) was slowly added thereto. The resulting solution was warmed to room temperature, followed by stirring for 2 hours. After the completion of the reaction was confirmed, 15% ammonium chloride aqueous solution (165 L) was added thereto, followed by stirring for 15 minutes. Then, the organic layer was separated, and concentrated under reduced pressure. Toluene (66 L) was added thereto, and warmed to 50° C., followed by cooling to 20° C. Heptane (16.5 L) was added thereto, followed by stirring for 1 hour. The obtained solid was filtered, and washed with heptane:toluene (1:1, 49.5 L), followed by vacuum drying at 20 to 30° C. to give a compound of formula (8a) (40.84 kg, 68.7%).

$^1$H NMR (300 MHz, CDCl$_3$): δ 7.80 (2H, d, J=8.1 Hz), 7.36 (2H, d, J=8.1 Hz), 5.88 (1H, d, J=3.6 Hz), 4.51 (1H, d, J=3.3 Hz), 4.38-4.30 (3H, m), 4.14 (1H, m), 2.46 (3H, s), 2.40 (1H, brs), 1.46 (3H, s), 1.30 (3H, s).

Example 2

Preparation of Compound of Formula (9)

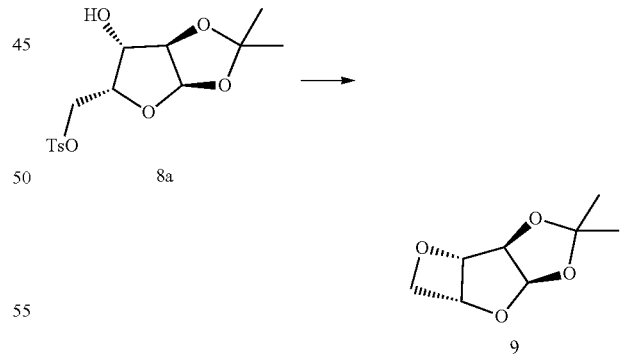

The compound of formula (8a) (40 kg) was dissolved in methanol (320 L), and potassium carbonate (24.1 kg) was added thereto. The resulting solution was warmed to 45 to 50° C., followed by stirring for 3 hours. The resulting solution was cooled to room temperature and filtered, and the filtrate was concentrated under reduced pressure. To the concentrated solution were added water (200 L) and methylene chloride (400 L), followed by stirring for 15 minutes, and the organic layer was separated. Sodium sulfate was added thereto, followed by filtration. The filtrate was concentrated under reduced pressure to give a compound of formula (9) (18.9 kg, 94.7%), which was used for the following reaction without additional purification.

$^1$H NMR (300 MHz, CDCl$_3$): δ 6.28 (1H, d, J=3.6 Hz), 5.20 (1H, d, J=3.9 Hz), 5.13-5.10 (1H, m), 4.76-4.72 (2H, m), 4.23 (1H, dd, J=2.4, 15.6 Hz), 1.42 (3H, s), 1.38 (3H, s).

Example 3

Preparation of Compound of Formula (10)

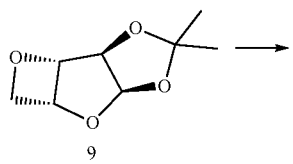

9

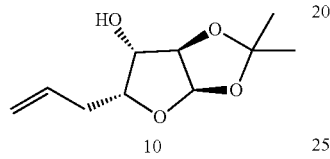

10

The compound of formula (9) (18.3 kg) was dissolved in tetrahydrofuran (47.6 L), and cooled to 0° C. Vinylmagnesium bromide (212.6 L) was added thereto, followed by heating to 70° C. and stirring for 17 hours. The resulting solution was cooled to 0° C., and 15% ammonium chloride aqueous solution (183 L) and ethyl acetate (183 L) were added thereto, followed by stirring for 15 minutes. The organic layer was separated, and washed with water (183 L). The organic layer was concentrated under reduced pressure, and toluene (36.6 L) and heptane (36.6 L) were added thereto, followed by stirring at 50° C. for complete dissolution. The resulting solution was cooled to 20° C., followed by stirring for 1 hour until solid was formed. Heptane (36.6 L) was added thereto, followed by additional stirring for 1 hour. The obtained solid was filtered, and washed with heptane:toluene (1:5, 36.6 L), followed by vacuum drying at 45° C. to give a compound of formula (10) (14.2 kg, 59.8%).

$^1$H NMR (300 MHz, CDCl$_3$): δ 5.93-5.79 (2H, m), 5.23-5.10 (2H, m), 4.51 (1H, d, J=3.6 Hz), 4.19 (1H, td, J=2.4, 7.4 Hz), 4.09 (1H, s), 2.58-2.37 (2H, m), 1.92 (1H, s, J=4.8 Hz), 1.50 (3H, s), 1.31 (3H, s).

Example 4

Preparation of Compound of Formula (11)

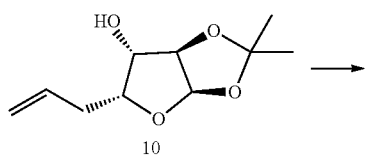

10

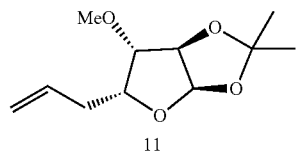

11

The compound of formula (10) (14.2 kg) was dissolved in dimethylformamide (71 L), and cooled to 0° C. Sodium hydride (3.68 kg) and tetrabutylammonium iodide (1.31 kg) was sequentially added thereto. Iodomethane (18.12 kg) was slowly added thereto, and stirred for 2 hours at 20 to 30° C. 15% ammonium chloride aqueous solution (71 L) and ethyl acetate (71 L) were added thereto, followed by stirring for 15 minutes. The organic layer was separated, washed twice with 15% ammonium chloride aqueous solution (71 L), and washed with water (71 L). The organic layer was concentrated under reduced pressure to give a compound of formula (11) (14.6 kg, 95.9%).

$^1$H NMR (300 MHz, CDCl$_3$): δ 5.89 (1H, d, J=3.9 Hz), 5.89-5.74 (1H, m), 5.19-5.06 (2H, m), 4.57 (1H, d, J=3.9 Hz), 4.18 (1H, td, J=3.0, 7.2 Hz), 3.57 (1H, d, J=3.0 Hz) 3.41 (3H, s), 2.49-2.43 (2H, m), 1.49 (3H, s), 1.32 (3H, s).

Example 5

Preparation of Compound of Formula (12)

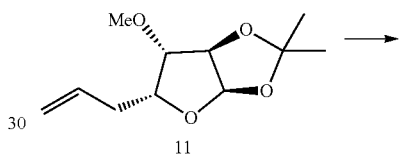

11

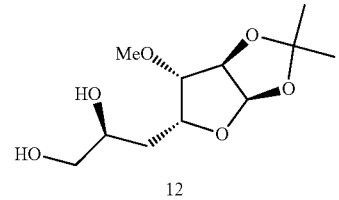

12

The compound of formula (11) (14.6 kg) was dissolved in butanol (1 L) and water (189.4 L), and (DHQ)$_2$AQN (291.4 g), potassium ferricyanide (76.12 kg) and potassium carbonate (32 kg) were added thereto, followed by cooling to −5 to 0° C. Potassium osmate dihydrate (75.2 g) was added with maintaining the temperature of 0° C. or lower, followed by stirring for 18 hours. To the resulting solution was added sodium thiosulfate (37.6 kg), followed by warming to room temperature and stirring for 15 hours. Toluene (218.6 L) was added thereto, and stirred for 15 minutes. The organic layer was separated, and 20% sodium chloride aqueous solution (145.7 L) was added to the organic layer, followed by stirring for 15 minutes. The organic layer was separated, and concentrated under reduced pressure to give a compound of formula (12) (16.88 kg), which was used for the following reaction without additional purification.

$^1$H NMR (300 MHz, CDCl$_3$): δ 5.90-5.87 (1H, m), 4.59-4.57 (1H, m), 4.42-4.36 (1H, m), 3.96-3.89 (1H, m), 3.70-3.62 (2H, m), 3.57-3.47 (1H, m), 3.42 (3H, s), 2.00-1.69 (2H, m), 1.50 (3H, s), 1.33 (3H, s).

Example 6

Preparation of Compound of Formula (13a)

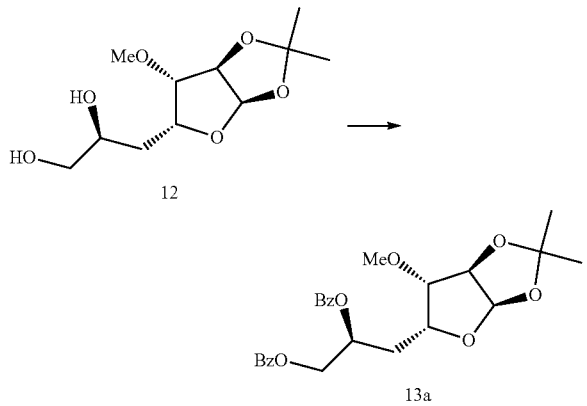

To the compound of formula (12) (16.9 kg) were added toluene (168.8 L), N-methylmorpholine (20.63 kg) and dimethylaminopyridine (1.66 kg), followed by cooling to 5° C. or lower. Benzoyl chloride (23.7 L) was added dropwise thereto with maintaining the temperature of 25° C. or lower. The resulting solution was heated to 75° C. and stirred for 6 hours. After cooling to 0° C. or lower, 1N hydrochloric acid (84.4 L) was slowly added dropwise thereto, followed by stirring for 15 minutes. The organic layer was separated, and washed with 20% sodium chloride aqueous solution (50.64 L), 5% sodium hydrogen carbonate aqueous solution (50.64 L), and water (50.64 L) sequentially. The organic layer was concentrated under reduced pressure to give a compound of formula (13a) (31.04 kg), which was used for the following reaction without additional purification.

$^1$H NMR (300 MHz, CDCl$_3$): δ 8.06-7.99 (4H, m), 7.58-7.48 (2H, m), 7.45-7.37 (4H, m), 5.89-5.87 (1H, m), 5.68-5.56 (1H, m), 4.69-4.50 (3H, m), 4.34-4.33 (1H, m), 3.70 (0.71H, d, J=3.2), 3.60 (0.29H, d, J=3.1) 3.42 (2.09H, s), 3.39 (0.91H, s), 2.33-2.19 (2H, m), 1.40 (3H, s), 1.30 (3H, s).

Example 7

Preparation of Compound of Formula (14a)

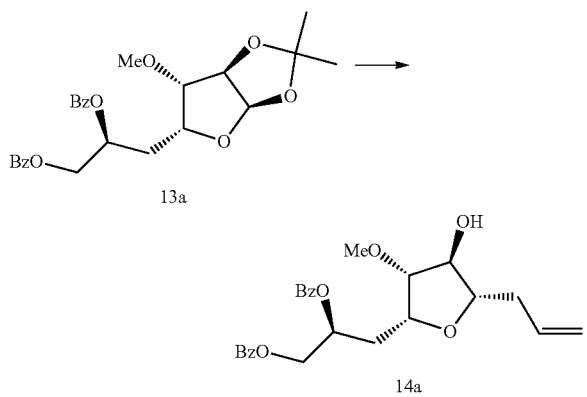

To a reactor (1) were added 1M titanium tetrachloride (306 L) and toluene (93.12 L), followed by cooling to 0° C. or lower. Titanium isopropoxide (30.20 L) was added dropwise thereto, with maintaining the temperature of 25° C. or lower. The resulting solution was warmed to room temperature and stirred for 0.5 hour. To a reactor (2) were added the compound of formula (13a) (31.04 kg), toluene (217.28 L), and allyltrimethylsilane (51.87 L), followed by stirring for 10 minutes at room temperature, and cooling to 0° C. Then, they were added dropwise to the reactor (1) with maintaining the temperature of 25° C. or lower. The resulting solution was additionally stirred at room temperature for 1 hour, and then cooled to −5° C. or lower. 1N hydrochloric acid (186.24 L) was added with maintaining the temperature of 25° C. or lower, followed by stirring for 15 minutes. The organic layer was separated, and washed with 1N hydrochloric acid (93.12 L) and water (93.12 L) sequentially. The organic layer was concentrated, and isopropanol (62.08 L) was added thereto, followed by additional concentration under reduced pressure. Isopropanol (31.04 L) was added thereto, stirred at 60° C. for complete dissolution, and then cooled to 20° C. The resulting solution was additionally stirred for 1 hour until the solid was obtained. The obtained solid was filtered, and vacuum-dried at 30° C. to give a compound of formula (14a) (32.33 kg, 32.33%).

$^1$H NMR (300 MHz, CDCl$_3$): δ 8.06-7.99 (4H, m), 7.56-7.51 (2H, m), 7.45-7.38 (4H, m), 5.89-5.75 (1H, m), 5.67-5.59 (1H, m), 5.16-5.06 (2H, m), 4.58-4.55 (2H, m), 4.17-4.15 (1H, m), 3.95-3.97 (1H, m), 3.67-3.62 (2H, m), 3.42 (3H, s), 2.49-2.32 (2H, m), 2.22 (2H, t, J=6.6 Hz).

Example 8

Preparation of Compound of Formula (15a)

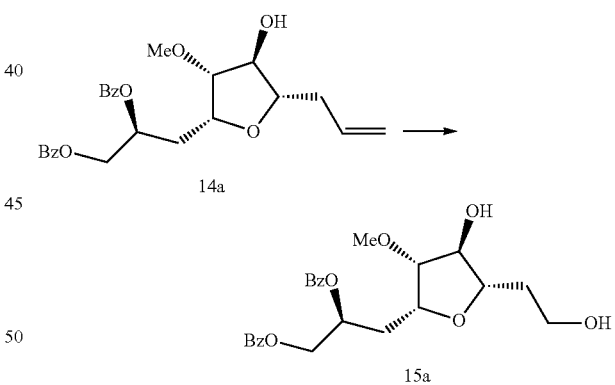

The compound of formula (14a) (10.1 kg) was dissolved in acetonitrile (130 L), and then water (130 L), potassium ferricyanide (26.4 kg), potassium carbonate (11.1 kg), and potassium osmate (84 g) were sequentially added thereto, followed by stirring at room temperature for 18 hours. Sodium thiosulfate (12.7 kg) was added thereto, followed by additional stirring for 6 hours. Ethyl acetate (100 L) was added thereto, and stirred for 15 minutes or more, and then the organic layer was separated. The organic layer was washed with water (50 L). The separated organic layer was concentrated under reduced pressure. Methylene chloride (109 L) and 8% sodium hydrogen carbonate aqueous solution (5.44 L) were added thereto, and cooled to −5° C. Sodium periodate (0.43 kg) was added thereto, and stirred at room temperature for 1.5 hours. The resulting solution was filtered, and the filtrate was washed with 15% sodium thiosulfate aqueous solution. The separated organic layer was dehydrated with sodium sulfate, and then filtered, followed by concentration under reduced pressure. Methanol (80 L) was added thereto for dissolution, followed by cooling to −5° C. Sodium borohydride (1 kg) was added thereto with maintaining the temperature of 5° C. or lower. The resulting solution was stirred at −5° C. for 1 hour, and 15% ammonium chloride aqueous solution (106 L) was slowly added thereto. Methanol was concentrated under reduced pressure by 80%, and methylenechloride (53 L) was added thereto, followed by stirring for 15 minutes or more. The organic layer was separated and concentrated under reduced pressure to give a compound of formula (15a) (10.22 kg), which was used for the following reaction without additional purification.

$^1$H NMR (300 MHz, CDCl$_3$): δ 8.06-7.99 (4H, m), 7.58-7.51 (2H, m), 7.45-7.38 (4H, m), 5.68-5.60 (1H, m), 4.61-4.51 (2H, m), 4.18-4.12 (1H, m), 3.95 (1H, dd, J=2.4, 5.7) 3.87-3.80 (1H, m), 3.76-3.62 (3H, m), 3.41 (3H, s), 2.23-2.17 (2H, m), 1.93-1.86 (2H, m).

Example 9

Preparation of Compound of Formula (16a)

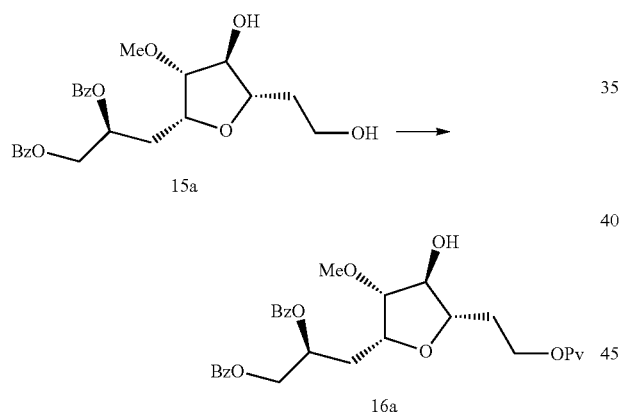

To the compound of formula (15a) (10.22 kg) were added methylenechloride (102 L) and pyridine (3.72 L) for dissolution, followed by cooling to −5 to 0° C. Pivaloyl chloride (4.24 L) was added dropwise thereto, followed by stirring at 20 to 30° C. for 6 hours or more. 15% ammonium chloride aqueous solution (102 L) was added thereto and stirred for 15 minutes or more. The organic layer was separated, and washed with 1N hydrochloric acid (51 L) and water (51 L) sequentially. The organic layer was concentrated under reduced pressure and subjected to chromatography (ethyl acetate:n-hexane=1:4) to give a compound of formula (16a) (8.39 kg, 69.22%).

$^1$H NMR (300 MHz, CDCl$_3$): δ 8.06-7.99 (4H, m), 7.58-7.51 (2H, m), 7.45-7.38 (4H, m), 5.66-5.58 (1H, m), 4.62-4.51 (2H, m), 4.32-4.24 (1H, m), 4.19-4.03 (2H, m), 4.00-3.99 (1H, m), 3.67-3.61 (2H, m), 3.40 (3H, s), 2.21 (2H, t, J=6.6 Hz), 1.98-1.89 (2H, m), 1.19 (9H, s).

Example 10

Preparation of Compound of Formula (17a)

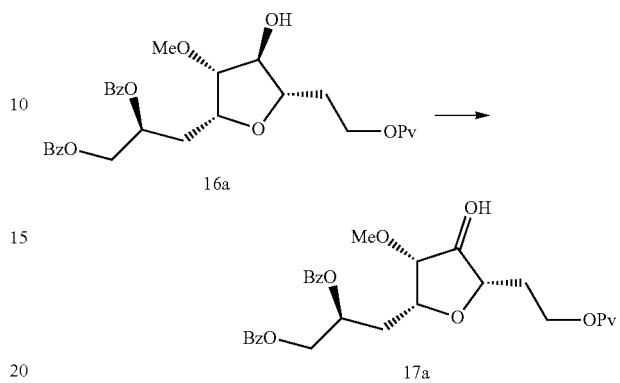

To the compound of formula (16a) (8.39 kg) was added methylenechloride (125.9 L) for dissolution. Then, Dess-Martin periodinane (13.46 kg) and sodium hydrogen carbonate (2.66 kg) were added thereto, followed by stirring at room temperature for about 3 hours. 10% sodium thiosulfate aqueous solution (83.9 L) and 8% sodium hydrogen carbonate aqueous solution (83.9 L) were slowly added thereto, followed by stirring for 15 minutes or more. The organic layer was separated and washed with 8% sodium hydrogen carbonate aqueous solution (83.9 L). The organic layer was filtered and concentrated under reduced pressure to give a compound of formula (17a) (8.36 kg), which was used for the following reaction without additional purification.

$^1$H NMR (300 MHz, CDCl$_3$): δ 8.06-8.00 (H, m), 7.60-7.53 (2H, m), 7.47-7.39 (4H, m), 5.68-5.61 (1H, m), 4.59 (2H, d, J=4.8 Hz), 4.24-4.11 (3H, m), 3.84 (1H, dd, J=3.6, 8.6 Hz), 3.61 (1H, d, J=4.5 Hz), 3.49 (3H, s), 2.40-2.23 (2H, m), 2.17-2.04 (1H, m), 1.95-1.84 (1H, m), 1.17 (9H, s).

Example 11

Preparation of Compound of Formula (18a)

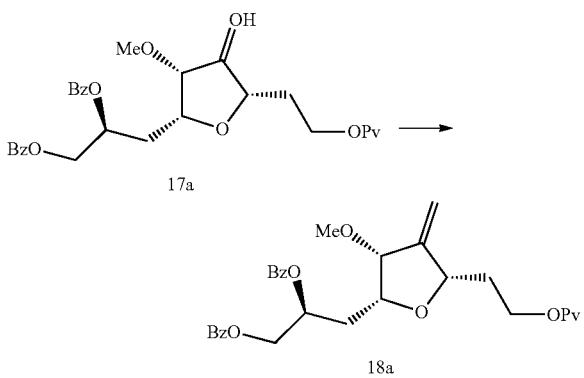

Nysted reagent (36.2 kg) and tetrahydrofuran (66.88 L) were cooled to −10° C., and the compound of formula (17a) (8.36 kg) dissolved in tetrahydrofuran (16.72 L) was added thereto. 1M titanium tetrachloride (17.46 L) was added dropwise thereto with maintaining the temperature of 5° C.

or lower. The resulting solution was warmed to room temperature and stirred for 1.5 hours. The resulting solution was cooled to −10° C., and then 1N hydrochloric acid (83.6 L) and ethyl acetate (83.6 L) were added thereto, followed by stirring for 15 minutes or more. The organic layer was separated and washed three times with water (83.6 L). The organic layer was concentrated under reduced pressure and subjected to chromatography (ethyl acetate:n-hexane=1:4) to give a compound of formula (18a) (5.23 kg, 62.79%).

$^1$H NMR (300 MHz, CDCl$_3$): δ 8.06-7.99 (4H, m), 7.58-7.51 (2H, m), 7.45-7.38 (4H, m), 5.68-5.60 (1H, m), 5.27 (1H, d, J=1.8 Hz), 5.14 (1H, brs), 4.55-4.55 (2H, m), 4.37 (1H, t, J=6), 4.18-4.09 (2H, m), 3.98-3.93 (2H, m), 3.30 (3H, s), 2.30-2.24 (2H, m), 1.92 (2H, q, J=6.6), 1.18 (9H, s).

Example 12

Preparation of Compound of Formula (19a)

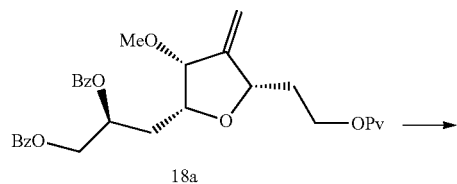

18a

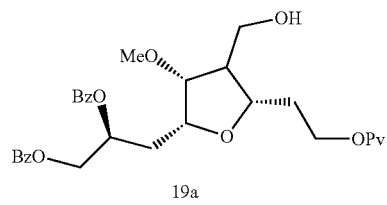

19a 1M borane tetrahydrofuran complex solution (21.6 L) was cooled to −5° C., and 2,3-dimethyl-2-butene (2.57 L) diluted with tetrahydrofuran (19.03 L) was added thereto, followed by stirring for 2 hours. The compound of formula (18a) (5.15 kg) was dissolved in tetrahydrofuran (43.2 L), and then added dropwise thereto at 0° C. or lower. The resulting solution was warmed to room temperature, followed by additional stirring for 1 hour or more. The resulting solution was cooled to −10° C. or lower, and then warmed to 20 to 30° C. with adding dropwise water (51.5 L) thereto. Sodium perborate tetrahydrate (6.65 kg) was added thereto, followed by stirring for 15 hours or more. The resulting solution was filtered, and water (25.75 L) and ethyl acetate (51.5 L) were added thereto, followed by stirring for 15 minutes or more. The organic layer was separated and washed with 20% ammonium chloride aqueous solution (25.75 L). The organic layer was concentrated under reduced pressure and subjected to chromatography (ethyl acetate:n-hexane=1:3) to give a compound of formula (19a) (4.62 kg, 86.7%).

$^1$H NMR (300 MHz, CDCl$_3$): δ 8.07-7.99 (4H, m), 7.58-7.51 (2H, m), 7.46-7.38 (4H, m), 5.70-5.62 (1H, m), 4.63-4.54 (2H, m), 4.23-3.74 (7H, m), 3.51 (3H, s), 2.58-2.49 (1H, m), 2.28-2.14 (3H, m), 1.99-1.87 (1H, m), 1.80-1.69 (1H, m), 1.17 (9H, s).

Example 13

Preparation of Compound of Formula (20a)

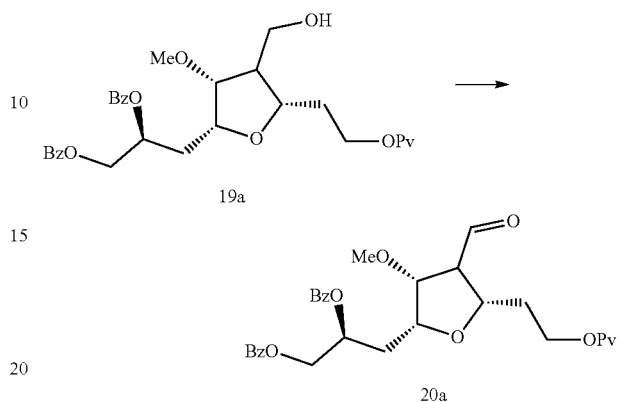

To the compound of formula (19a) (4.56 kg) was added methylenechloride (22.8 L) for dissolution, followed by cooling to 5 to 10° C. Dess-Martin periodinane (7.13 kg) and sodium hydrogen carbonate (1.41 kg) were added thereto, followed by stirring at room temperature for about 1 hour. 10% sodium thiosulfate aqueous solution (45.6 L) and 8% sodium hydrogen carbonate aqueous solution (45.6 L) were slowly added thereto, and stirred for 30 minutes or more. The organic layer was separated and washed with 8% sodium hydrogen carbonate aqueous solution (67.7 L). The organic layer was filtered with sodium sulfate (2.3 kg), and then concentrated under reduced pressure to give a compound of formula (20a) (4.54 kg), which was used for the following reaction without additional purification.

$^1$H NMR (300 MHz, CDCl$_3$): δ 9.8 (1H, d, J=1.8), 8.06-7.99 (4H, m), 7.58-7.51 (2H, m), 7.46-7.38 (4H, m), 5.67-5.59 (1H, m), 4.61-4.51 (2H, m), 4.21-4.04 (4H, m), 3.94-3.88 (1H, m), 3.35 (3H, s), 2.90-2.86 (1H, m), 2.23 (2H, t, J=6.7 Hz), 2.08-1.89 (2H, m), 1.18 (9H, s).

Example 14

Preparation of Compound of Formula (21a)

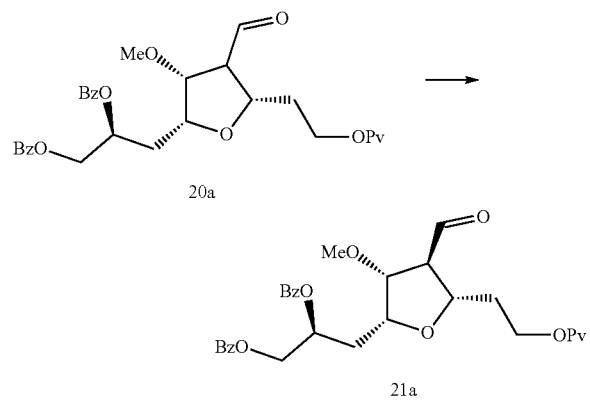

The compound of formula (20a) (4.54 kg) was dissolved in methylenechloride (45.4 L), and triethylamine (1.3 L) was added thereto, followed by stirring at room temperature for about 17 hours. Water (45.4 L) was added thereto, followed by stirring for 15 minutes or more. The organic layer was separated and washed with 1N hydrochloric acid (45.4 L) and water (45.4 L) sequentially. The organic layer was concentrated under reduced pressure to give a compound of formula (21a) (4.56 kg), which was used for the following reaction without additional purification.

$^1$H NMR (300 MHz, CDCl$_3$): δ 9.8 (1H, d, J=1.8), 8.06-7.99 (4H, m), 7.58-7.51 (2H, m), 7.46-7.38 (4H, m), 5.67-5.59 (1H, m), 4.61-4.51 (2H, m), 4.21-4.04 (4H, m), 3.94-3.88 (1H, m), 3.35 (3H, s), 2.90-2.86 (1H, m), 2.23 (2H, t, J=6.7 Hz), 2.08-1.89 (2H, m), 1.18 (9H, s).

Example 15

Preparation of Compound of Formula (22a)

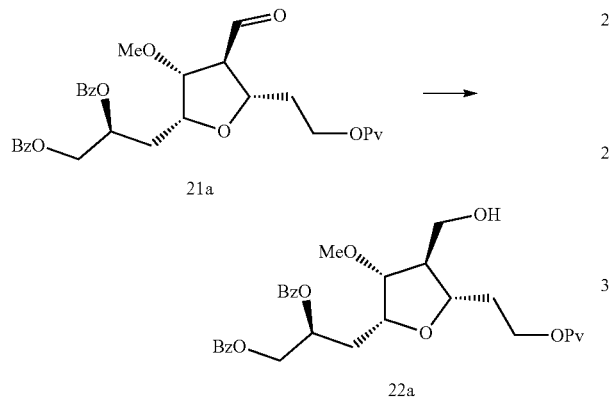

To the compound of formula (21a) (4.56 kg) was added methanol (45.6 L) for dissolution, followed by cooling to −10° C. Sodium borohydride (476 g) was added thereto with maintaining the temperature of 5° C. or lower, followed by stirring at 0° C. for about 1 hour. 15% ammonium chloride aqueous solution (45.6 L) was added dropwise thereto, and then methylene chloride (45.6 L) was added thereto, followed by stirring for 30 minutes. The organic layer was separated, concentrated under reduced pressure, and subjected to chromatography (ethyl acetate:n-hexane=1:3) to give a compound of formula (22a) (3.16 kg, 69.3%).

$^1$H NMR (300 MHz, CDCl$_3$): δ 8.06-7.99 (4H, m), 7.58-7.51 (2H, m), 7.45-7.38 (4H, m), 5.66-5.59 (1H, m), 4.62-4.51 (2H, m), 4.21-4.04 (2H, m), 3.92-3.86 (1H, m), 3.70-3.68 (1H, m), 3.64-3.60 (2H, m), 3.33 (3H, s), 2.23 (2H, t, J=6.6 Hz), 2.12 (1H, qd, J=1.8, 6.8), 1.97-1.89 (3H, m), 1.17 (9H, s).

Example 16

Preparation of Compound of Formula (23a)

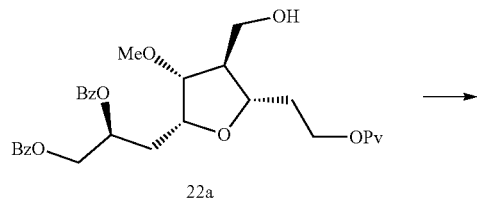

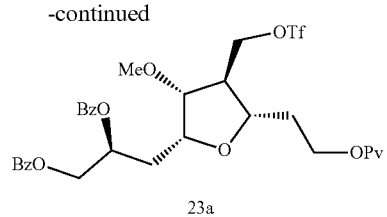

The compound of formula (22a) (3.16 kg) was dissolved in methylenechloride (31.6 L) and pyridine (0.76 L), and then cooled to 0° C. Trifluoromethanesulfonic anhydride (1.47 L) was added dropwise thereto, followed by stirring for 1 hour. The resulting solution was washed with 1N hydrochloric acid (31.6 L) and 8% sodium hydrogen carbonate aqueous solution (31.6 L) sequentially. The separated organic layer was concentrated under reduced pressure to give a compound of formula (23a) (3.93 kg), which was used for the following reaction without additional purification.

$^1$H NMR (300 MHz, CDCl$_3$): δ 8.06-7.97 (4H, m), 7.59-7.52 (2H, m), 7.46-7.34 (4H, m), 5.66-5.55 (1H, m), 4.56 (2H, d, J=5.4 Hz), 4.47 (2H, d, J=6.9 Hz), 4.21-4.03 (2H, m), 3.95-3.89 (1H, m), 3.74-3.72 (1H, m), 3.63 (1H, q, J=6.6 Hz), 3.34 (3H, s), 2.37 (1H, qd, J=2.2, 6.9 Hz), 2.23 (2H, t, J=6.6 Hz), 1.95 (2H, q, J=6.4 Hz), 1.18 (9H, s).

Example 17

Preparation of Compound of Formula (24a)

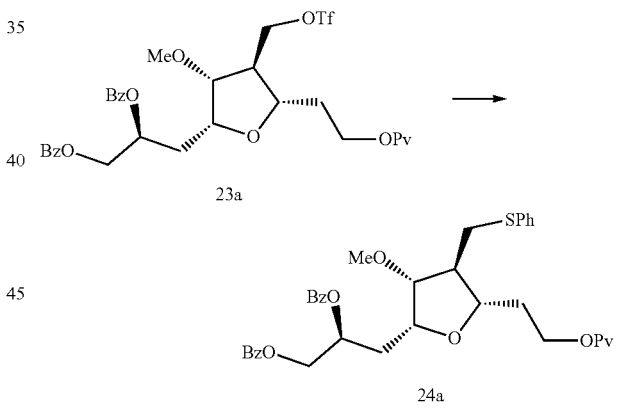

To the compound of formula (23a) (3.93 kg) was added tetrahydrofuran (39.3 L), followed by cooling to −5 to 0° C. 1M lithium thiophenolate (9.3 L) was added thereto, followed by stirring for about 2 hours. 15% ammonium chloride aqueous solution (39.3 L) and ethyl acetate (39.3 L) were added thereto, followed by stirring for 15 minutes or more. The organic layer was separated, concentrated under reduced pressure, and subjected to chromatography (ethyl acetate:n-hexane=1:7) to give a compound of formula (24a) (1.59 kg, 43%).

$^1$H NMR (300 MHz, CDCl$_3$): δ 8.07-7.99 (4H, m), 7.56-7.52 (2H, m), 7.51-7.38 (4H, m), 7.32-7.27 (4H, m), 7.22-7.16 (1H, m), 5.64-5.57 (1H, m), 4.16-4.03 (2H, m), 3.98-3.92 (2H, m), 3.71-3.65 (2H, m), 3.29 (3H, s), 2.92 (2H, d, J=7.5 Hz), 2.23 (1H, t, J=6.3 Hz), 2.18-2.11 (2H, m), 1.97-1.83 (2H, m), 1.18 (9H, s).

Example 18

Preparation of Compound of Formula (25)

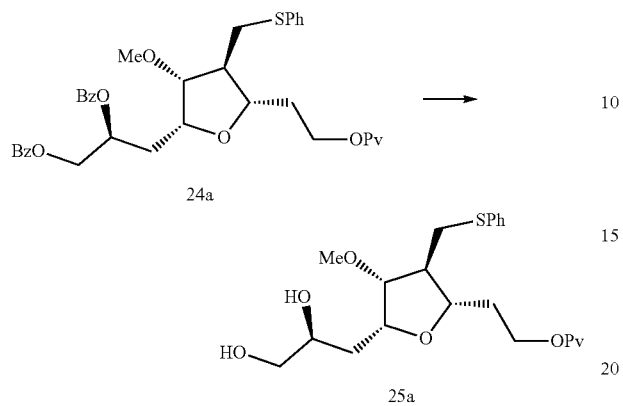

The compound of formula (24a) (1.59 kg) was dissolved in methanol (16 L), and 7-8% magnesium methoxide (7.2 L) was added thereto, followed by stirring at room temperature for about 15 hours. 15% ammonium chloride aqueous solution (16 L) was added thereto, and methanol was concentrated. The resulting solution was extracted with methylenechloride (16 L), and the organic layer was dehydrated with sodium sulfate, filtered, and concentrated under reduced pressure to give a compound of formula (25a) (1.07 kg), which was used for the following reaction without additional purification.

$^1$H NMR (300 MHz, CDCl$_3$): δ 7.36-7.28 (4H, m), 7.24-7.18 (1H, m), 4.14 (2H, t, J=6.6 Hz), 4.06-4.00 (1H, m), 3.80-3.74 (1H, m), 3.68-3.62 (2H, m), 3.56-3.3.50 (1H, m), 3.28 (3H, s), 3.03-2.90 (2H, m), 2.40 (1H, t, J=6 Hz), 2.21-2.14 (1H, m), 1.99-1.86 (3H, m), 1.81-1.74 (1H, m), 1.20 (9H, s).

Example 19

Preparation of Compound of Formula (26a)

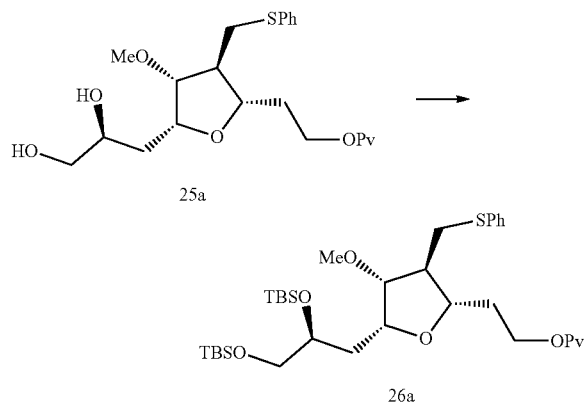

The compound of formula (25a) (1.07 kg) was dissolved in methylenechloride (11 L), and imidazole (0.854 kg) and t-butyldimethylsilyl chloride (1.13 kg) were sequentially added thereto, followed by stirring at 20 to 30° C. for 16 hours. The resulting solution was washed twice with water (11 L), and sodium sulfate was added to the separated organic layer, followed by filtration and concentration. The resulting residue was subjected to chromatography (ethyl acetate:n-hexane=1:12) to give a compound of formula (26a) (1.16 kg, 70.7%).

$^1$H NMR (300 MHz, CDCl$_3$): δ 7.34-7.27 (4H, m), 7.23-7.17 (1H, m), 4.20-4.07 (2H, m), 3.96-3.91 (1H, m), 3.78 (1H, qui, J=5.1 Hz), 3.67-3.61 (1H, m), 3.60-3.55 (1H, m), 3.48 (1H, dd, J=5.1, 10.4 Hz), 3.26 (3H, s), 3.00-2.84 (2H, m), 2.15-2.09 (1H, m), 1.98-1.81 (3H, m), 1.78-1.71 (1H, m), 1.19 (9H, s), 0.88 (9H, s), 0.87 (9H, s), 0.07 (6H, d, J=3.9 Hz), 0.04 (6H, d, J=1.8 Hz).

Example 20

Preparation of Compound of Formula (27a)

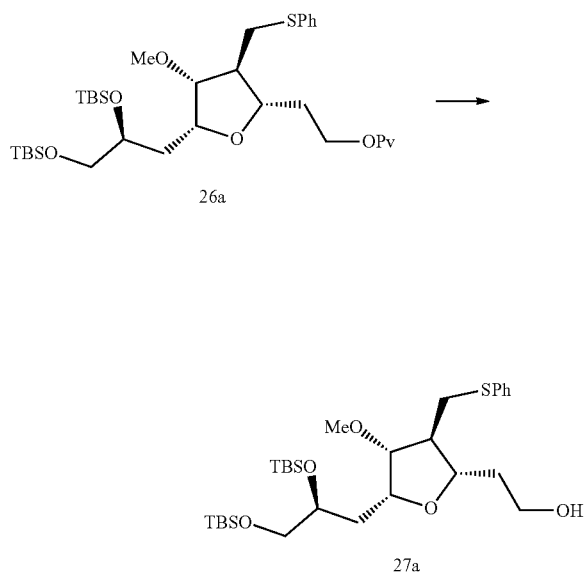

The compound of formula (26a) (1.16 kg) was dissolved in tetrahydrofuran (11.6 L), followed by cooling to −10° C. or lower. 1.2M DIBAL-H (3.2 L) was added dropwise thereto with maintaining the temperature of 5° C. or lower, followed by stirring for 2 hours. 1N hydrochloric acid (11.6 L) and ethyl acetate (11.6 L) were added thereto, followed by stirring for 15 minutes. The organic layer was separated, and washed with water (11.6 L). Sodium sulfate was added to the separated organic layer, followed by filtration and concentration under reduced pressure. The resulting residue was subjected to chromatography (ethyl acetate:n-hexane=1:5) to give a compound of formula (27a) (0.8 kg, 79.9%).

$^1$H NMR (300 MHz, CDCl$_3$): δ 7.38-7.23 (4H, m), 7.23-7.18 (1H, m), 3.97-3.92 (1H, m), 3.82-3.72 (4H, m), 3.60-3.55 (2H, m), 3.48 (1H, dd, J=5.4, 10.2 Hz), 3.28 (3H, s), 3.01-2.88 (2H, m), 2.52 (1H, brs), 2.24-2.17 (1H, m), 2.04-1.89 (2H, m), 1.87-1.74 (2H, m), 0.89 (9H, s), 0.88 (9H, s), 0.07 (6H, d, J=3.3 Hz), 0.05 (6H, d, J=1.8 Hz).

Example 21

Preparation of Compound of Formula (6a)

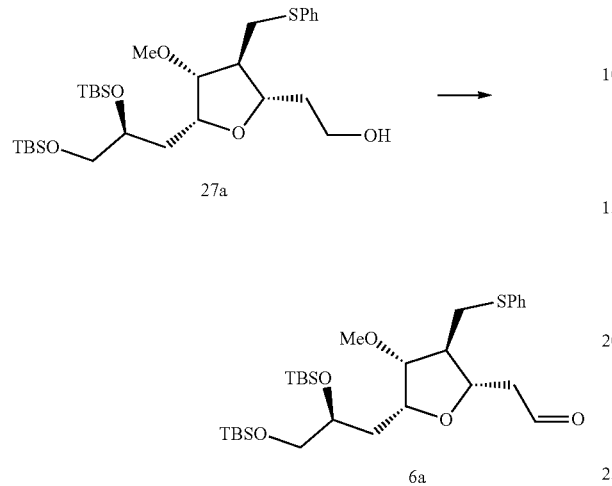

To the compound of formula (27a) (300 g) was added methylenechloride (6 L) for dissolution, followed by cooling to 5° C. Dess-Martin periodinane (236.2 g) and sodium hydrogen carbonate (85 g) were added thereto, followed by stirring at room temperature for about 4 hours. 10% sodium thiosulfate aqueous solution (3 L) and 9% sodium hydrogen carbonate aqueous solution (3 L) were slowly added thereto, followed by stirring for 15 minutes or more. The organic layer was separated, and sodium sulfate was added thereto, followed by filtration and concentration under reduced pressure. The resulting residue was subjected to chromatography (ethyl acetate:n-hexane=1:5) to give a compound of formula (6a) (234.2 g, 81.3%).

$^1$H NMR (300 MHz, CDCl$_3$): δ 9.75 (1H, t, J=1.8 Hz) 7.36-7.27 (4H, m), 7.23-7.21 (1H, m), 4.06-3.97 (2H, m), 3.82-3.74 (1H, m), 3.60-3.54 (2H, m), 3.47 (1H, dd, J=5.4, 10.2 Hz), 3.24 (3H, s), 3.10 (1H, dd, J=6.6, 13.2 Hz), 2.90 (1H, dd, J=8.7, 13.2 Hz), 2.81-2.64 (2H, m), 2.20-2.12 (1H, m), 1.99-1.91 (1H, m), 1.81-1.72 (1H, m), 0.89 (9H, s), 0.87 (9H, s), 0.07 (6H, d, J=3.6 Hz), 0.04 (6H, d, J=1.2 Hz).

Example 22

Preparation of Compound of Formula (29a)

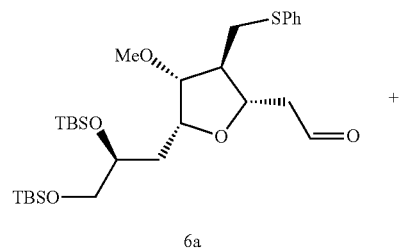

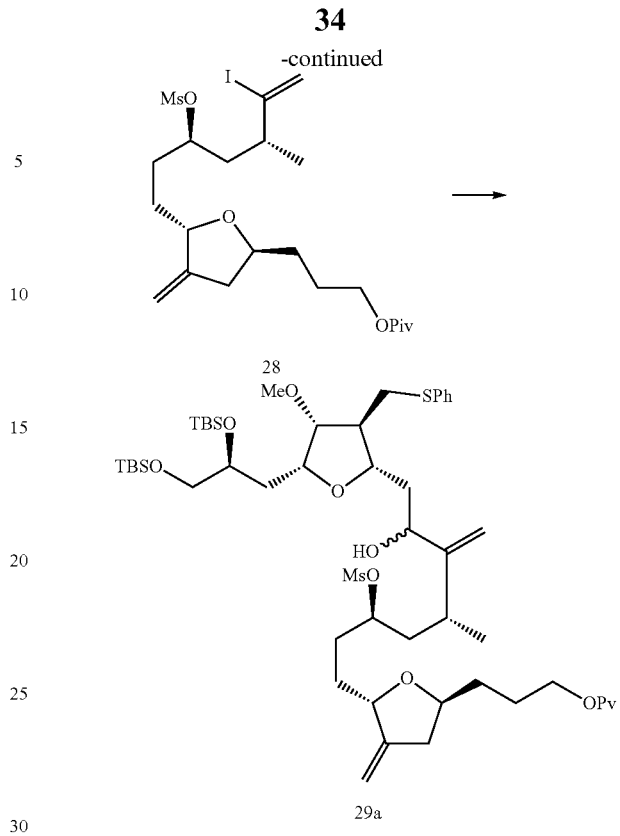

The oxygen concentration in the reactor was lowered to 200 ppm or lower with argon gas. (S)-N-(2-(4-isopropyl-4,5-dihydrooxazol-2-yl)-6-methylphenyl)methane sulfonimide (248 g) was dissolved in tetrahydrofuran (1.5 L), followed by cooling to 20° C. Chromium(II) chloride (103 g) and triethylamine (117 mL) were sequentially added thereto, followed by heating to 35° C. and stirring for 2 hours. The resulting solution was cooled to 5° C. or lower, and then nickel(II) chloride (2.8 g) was added thereto. The compound of formula (6a) (102 g) and the compound of formula (28) (100 g) were dissolved in tetrahydrofuran (0.5 L), and sequentially added thereto. The resulting solution was warmed to room temperature, followed by stirring for 20 hours. The resulting solution was cooled to 5° C., and ethylenediamine (157 mL) was added dropwise thereto, followed by stirring for 1 hour. The resulting solution was warmed to room temperature, and water (1 L) was added thereto, followed by stirring for 20 minutes. Then, heptane (2.5 L) was added thereto, followed by stirring for 30 minutes. The organic layer was separated, and the aqueous layer was re-extracted with methyl t-butyl ether (0.5 L). The combined organic layer was washed with 6% sodium bicarbonate solution (2 L) and 10% sodium chloride solution (1 L), respectively. The organic layer was concentrated, dissolved in heptane (2.6 L), and then cooled to −10° C., followed by stirring for 1 hour. The obtained solid was filtered. The filtrate was concentrated to give a compound of formula (29a) (179 g, 100%) without additional purification.

$^1$H NMR (300 MHz, CDCl$_3$): δ 7.17-7.43 (5H, m), 5.11-5.21 (1H, m), 4.95-5.00 (1H, m), 4.79-4.86 (3H, m), 4.36 (1H, bs), 4.24 (1H, d, J=8.7 Hz), 3.96-4.08 (4H, m), 3.72-3.79 (4H, m), 3.46-3.51 (4H, m), 3.27 (3H, s), 2.82-3.06 (4H, m), 2.67 (1H, dd, J=15.6, 5.4 Hz), 2.16-2.34 (3H, m), 1.40-2.01 (14H, m), 1.19 (9H, s), 1.09 (2H, d, J=6.9 Hz), 0.89 (9H, s), 0.88 (9H, s), 0.05-0.08 (12H, m)

Example 23

Preparation of Compound of Formula (30a)

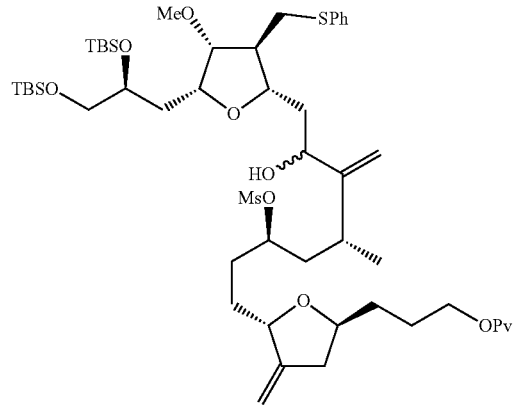

29a

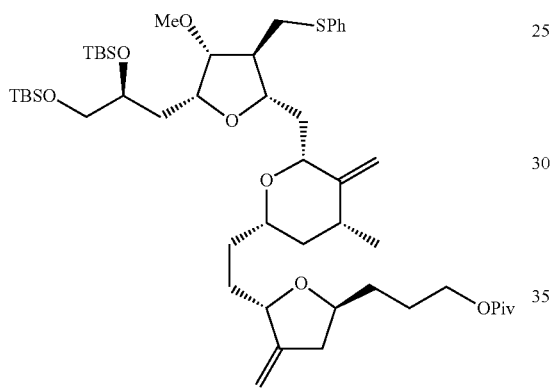

30a

The compound of formula (29a) (179 g) was dissolved in tetrahydrofuran (1 L), and cooled to −20° C. 0.5M potassium bis(trimethylsilyl)amide (1 L) was added dropwise thereto, followed by stirring for 1.5 hours. The resulting solution was warmed to 0° C., and then 7% sodium chloride solution (1 L) was added dropwise thereto. The resulting solution was warmed to room temperature, and heptane (1 L) was added thereto, followed by stirring for 20 minutes. The organic layer was separated, and the aqueous layer was re-extracted with methyl t-butyl ether (1 L). The combined organic layer was washed with 2% sodium chloride solution (0.5 L), and then the organic layer was concentrated. The resulting residue was subjected to chromatography (ethyl acetate:n-hexane=1:20) to give a compound of formula (30a) (84 g, 54.5%).

$^1$H NMR (300 MHz, CDCl$_3$): δ 7.38-7.29 (4H, m), 7.23-7.17 (1H, m), 4.96-4.95 (2H, m), 4.82-4.79 (2H, m), 4.08-3.89 (3H, m), 3.88-3.83 (1H, m), 3.81-3.69 (2H, m), 3.67-3.59 (1H, m), 3.58-3.3.53 (2H, m), 3.51-3.45 (2H, m), 3.28 (3H, s), 3.01 (1H, dd, J=4.9, 13.1 Hz), 2.80-2.73 (1H, m), 2.68-2.61 (1H, m), 2.27-2.07 (4H, s), 2.01-1.93 (2H, m), 1.84-1.48 (12H, m), 1.19 (9H, s), 1.07 (3H, d, J=6.4 Hz), 0.89 (9H, s), 0.88 (9H, s), 0.07 (6H, d, J=3.6 Hz), 0.04 (6H, d, J=1.6 Hz).

Example 24

Preparation of Compound of Formula (31a)

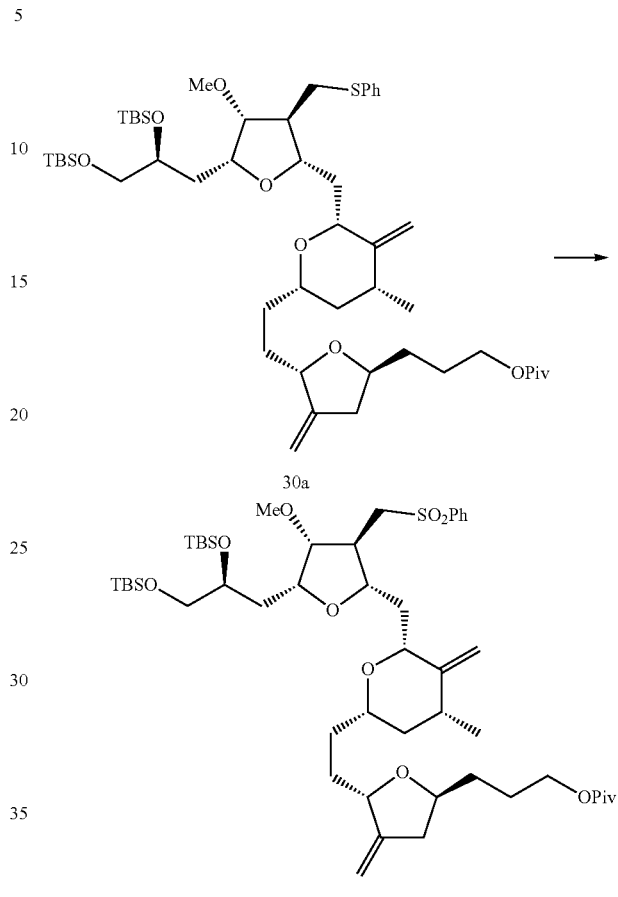

The compound of formula (30a) (102 g) and ammonium molybdate (9 g) were dissolved in ethanol (1 L) and cooled to 0° C. Urea hydrogen peroxide (64 g) was added thereto, followed by heating to room temperature and stirring for 12 hours. The resulting solution was cooled to 0° C., and then 8% sodium chloride solution (2 L) and 10% sodium thiosulfate (2 L) were added dropwise thereto. The resulting solution was stirred for 1 hour, ethyl acetate (1 L) was added thereto, followed by stirring for 30 minutes. Ethanol was concentrated, and the aqueous layer and the organic layer were separated. The aqueous layer was re-extracted with ethyl acetate (1 L), and then sodium sulfate was added to the combined organic layer, followed by filtration and concentration. The resulting residue was subjected to chromatography (ethyl acetate:n-hexane=1:20) to give a compound of formula (31a) (64 g, 61.6%).

$^1$H NMR (300 MHz, CDCl$_3$): δ 7.93-7.96 (2H, m), 7.57-7.71 (3H, m), 4.90 (1H, d, J=1.8 Hz), 4.85 (1H, s), 4.78 (1H, d, J=1.2 Hz), 4.67 (1H, d, J=1.8 Hz), 4.25 (br, 1H), 4.02-4.08 (2H, m), 3.92-4.00 (1H, m), 3.76-3.85 (3H, m), 3.64-3.71 (1H, m), 3.67-3.61 (2H, m), 3.36-3.51 (5H, m), 2.96-3.08 (2H, m), 2.52-2.66 (2H, m), 2.16-2.25 (3H, m), 1.35-2.04 (12H, m), 1.20 (9H, s), 1.03-1.08 (3H, m), 0.89 (18H, s), 0.88 (9H, s), 0.09 (6H, d, J=1.8 Hz), 0.04 (6H, d, J=1.8 Hz).

Example 25

Preparation of Compound of Formula (2a)

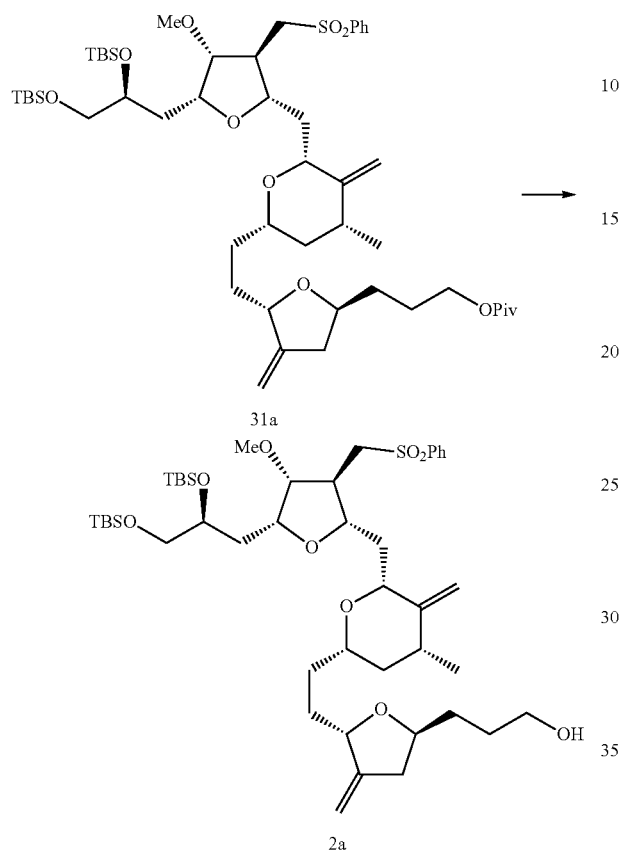

The compound of formula (31a) (240 g) was dissolved in toluene (1 L), and cooled to −65° C. 1.2M diisobutylaluminum hydride (0.5 L) was added dropwise thereto. Methanol (30 mL) was added dropwise thereto, followed by warming to room temperature. 1N hydrochloric acid (2.4 L) was added thereto, and then the organic layer was separated. The aqueous layer was re-extracted with methyl t-butyl ether (3 L). The combined organic layer was washed with 9% sodium bicarbonate solution (0.8 L), and the aqueous layer was re-extracted with methyl t-butyl ether (1 L). The combined organic layer was washed with 26% sodium chloride solution (0.8 L), and the aqueous layer was re-extracted with methyl t-butyl ether (0.5 L). The combined organic layer was concentrated, and the resulting residue was subjected to chromatography (heptane:methyl t-butyl ether=2:1) to give a compound of formula (2a) (201 g, 92%).

$^1$H NMR (300 MHz, CDCl$_3$): δ 7.93-7.96 (2H, m), 7.58-7.69 (3H, m), 4.91 (1H, d, J=2.1 Hz), 4.85 (1H, s), 4.77 (1H, s), 4.67 (1H, d, J=1.8 Hz), 4.30 (br, 1H), 3.94-4.02 (1H, m), 3.76-3.85 (3H, m), 3.55-3.71 (5H, m), 3.39-3.51 (5H, m), 3.20 (1H, s), 2.97-3.08 (2H, m), 2.52-2.66 (2H, m), 2.43-2.47 (1H, m), 2.16-2.28 (3H, m), 1.97-2.05 (1H, m), 1.37-1.92 (12H, m), 1.23-1.27 (2H, m), 1.04-1.11 (3H, m), 0.89 (18H, s), 0.88 (9H, s), 0.09 (6H, d, J=2.0 Hz), 0.04 (6H, d, J=1.9 Hz).

The invention claimed is:
1. A process for preparing a compound of the following formula (6), which comprises the steps of:
  (i) subjecting a primary hydroxy group of a compound of the following formula (7) to selective sulfonylation to obtain a compound of the following formula (8);
  (ii) subjecting the compound of the following formula (8) to cyclization to obtain a compound of the following formula (9);
  (iii) subjecting the compound of the following formula (9) to allylation to obtain a compound of the following formula (10);
  (iv) subjecting a hydroxy group of the compound of the following formula (10) to methylation to obtain a compound of the following formula (11);
  (v) subjecting an alkene group of the compound of the following formula (11) to stereoselective dehydroxylation to obtain a compound of the following formula (12);
  (vi) protecting a hydroxy group of the compound of the following formula (12) to obtain a compound of the following formula (13);
  (vii) subjecting the compound of the following formula (13) to Hosomi-Sakurai reaction to obtain a compound of the following formula (14);
  (viii) subjecting an alkene group of the compound of the following formula (14) to dehydroxylation, oxidation and reduction to obtain a compound of the following formula (15);
  (ix) selectively protecting a primary hydroxy group of the compound of the following formula (15) to obtain a compound of the following formula (16);
  (x) oxidizing a hydroxy group of the compound of the following formula (16) to obtain a compound of the following formula (17);
  (xi) subjecting the compound of the following formula (17) to methenylation to obtain a compound of the following formula (18);
  (xii) subjecting the compound of the following formula (18) to hydroboration and oxidation to obtain a compound of the following formula (19);
  (xiii) oxidizing a hydroxy group of the compound of the following formula (19) to obtain a compound of the following formula (20);
  (xiv) subjecting the compound of the following formula (20) to isomerization to obtain a compound of the following formula (21);
  (xv) reducing the compound of the following formula (21) to obtain a compound of the following formula (22);
  (xvi) subjecting a hydroxy group of the compound of the following formula (22) to sulfonylation to obtain a compound of the following formula (23);
  (xvii) substituting a leaving group of the compound of the following formula (23) with a sulfide to obtain a compound of the following formula (24);
  (xviii) selectively deprotecting a benzoyl or acetyl group of the compound of the following formula (24) to obtain a compound of the following formula (25);
  (xix) protecting a hydroxy group of the compound of the following formula (25) to obtain a compound of the following formula (26);
  (xx) deprotecting a pivaloyl group of the compound of the following formula (26) to obtain a compound of the following formula (27); and
  (xxi) oxidizing a hydroxy group of the compound of the following formula (27):

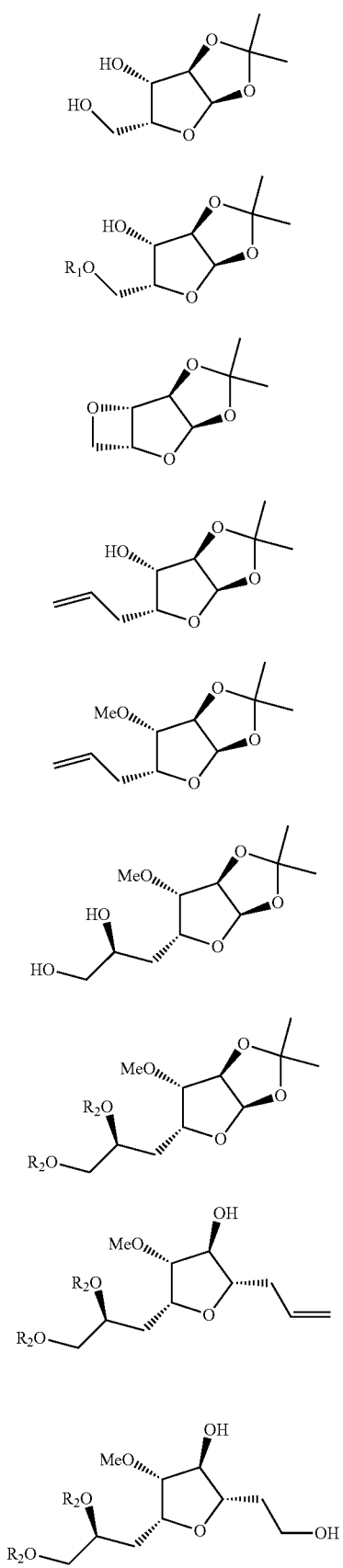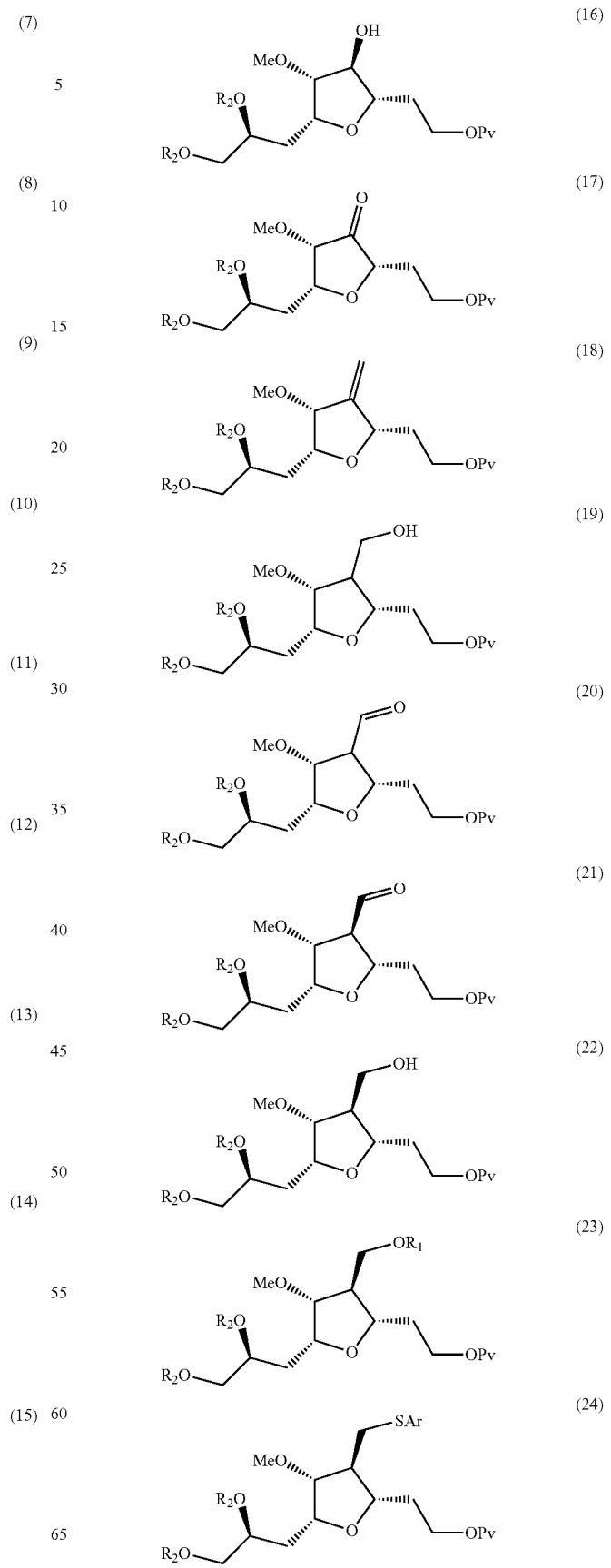

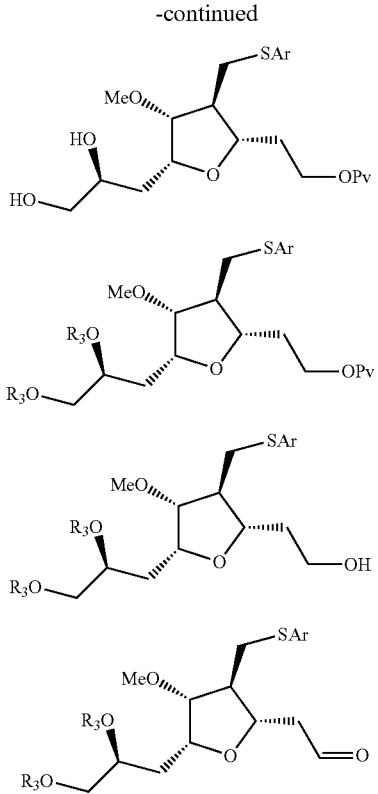

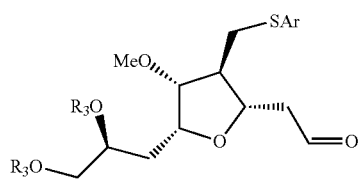

wherein,
$R_1$ represents a leaving group selected from the group consisting of p-toluenesulfonyl, methanesulfonyl, and trifluoromethanesulfonyl,
$R_2$ represents benzoyl or acetyl,
Pv represents pivaloyl,
Ar represents aryl, and
$R_3$ represents a silyl protecting group selected from the group consisting of trimethylsilyl (TMS), triethylsilyl (TES), t-butyldimethylsilyl (TBS), and t-butyldiphenylsilyl (TBDPS).

2. The process according to claim 1, wherein the sulfonylation of step (i) is carried out by reacting the compound of formula (7) with p-toluenesulfonyl halide, methanesulfonyl halide, or trifluoromethanesulfonic anhydride under a basic condition.

3. The process according to claim 1, wherein the allylation of step (iii) is carried out using a Grignard reagent.

4. The process according to claim 1, wherein the methylation of step (iv) is carried out by reacting the compound of formula (10) with methyl halide under a basic condition.

5. The process according to claim 1, wherein the protection of step (vi) is carried out by reacting the compound of formula (12) with benzoyl halide or acetyl halide under a basic condition.

6. The process according to claim 1, wherein the Hosomi-Sakurai reaction of step (vii) is carried out by reacting the compound of formula (13) with allylsilane in the presence of a Lewis acid.

7. The process according to claim 1, wherein the protection of step (ix) is carried out by reacting the compound of formula (15) with pivaloyl halide under a basic condition.

8. The process according to claim 1, wherein the sulfonylation of step (xvi) is carried out by reacting the compound of formula (22) with p-toluenesulfonyl halide, methanesulfonyl halide, or trifluoromethanesulfonic anhydride under a basic condition.

9. The process according to claim 1, wherein the substitution of step (xvii) is carried out using lithium thiophenolate.

10. The process according to claim 1, wherein the protection of step (xix) is carried out by reacting the compound of formula (25) with t-butyldimethylsilyl chloride, triethylsilyl trifluoromethanesulfonate or chlorotriethylsilane under a basic condition.

11. A compound of the following formula (6):

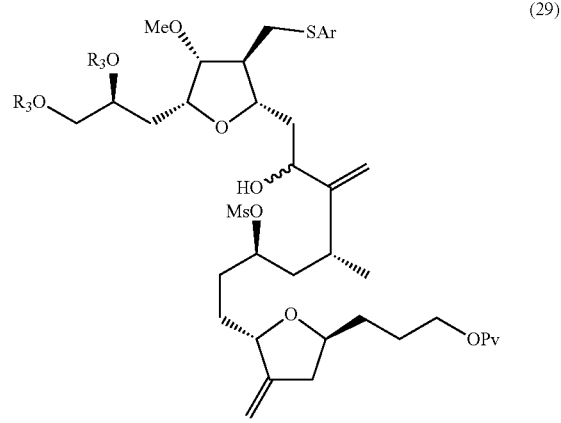

wherein,
$R_3$ represents a silyl protecting group selected from the group consisting of trimethylsilyl (TMS), triethylsilyl (TES), t-butyldimethylsilyl (TBS), and t-butyldiphenylsilyl (TBDPS), and
Ar represents aryl.

12. A compound of the following formula (29):

wherein,
$R_3$ represents a silyl protecting group selected from the group consisting of trimethylsilyl (TMS), triethylsilyl (TES), t-butyldimethylsilyl (TBS), and t-butyldiphenylsilyl (TBDPS),
Ar represents aryl,
Ms represents methanesulfonyl, and
Pv represents pivaloyl.

13. The compound of according to claim 12,
wherein,
$R_3$ represents t-butyldimethylsilyl, and
Ar represents phenyl.

* * * * *